United States Patent
Ryde et al.

(10) Patent No.: US 9,974,748 B2
(45) Date of Patent: *May 22, 2018

(54) REDUCTION OF FLAKE-LIKE AGGREGATION IN NANOPARTICULATE ACTIVE AGENT COMPOSITIONS

(71) Applicant: Alkermes Pharma Ireland Limited, Dublin (IE)

(72) Inventors: Niels P. Ryde, Malvern, PA (US); Peter Snyder, King of Prussia, PA (US); Wei Liu, Exton, PA (US); David M. Slifer, Downingtown, PA (US)

(73) Assignee: Alkermes Pharma Ireland Limited, Dublin (IE)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/130,396

(22) Filed: Apr. 15, 2016

(65) Prior Publication Data

US 2016/0228372 A1 Aug. 11, 2016

Related U.S. Application Data

(60) Continuation of application No. 14/133,191, filed on Dec. 18, 2013, now Pat. No. 9,345,665, which is a division of application No. 12/788,196, filed on May 26, 2010, now abandoned.

(60) Provisional application No. 61/181,641, filed on May 27, 2009.

(51) Int. Cl.

| | |
|---|---|
| *A61K 9/16* | (2006.01) |
| *A61K 9/00* | (2006.01) |
| *A61K 9/14* | (2006.01) |
| *A61K 31/5415* | (2006.01) |
| *A61K 9/10* | (2006.01) |
| *A61K 47/02* | (2006.01) |
| *A61K 47/10* | (2017.01) |
| *A61K 47/26* | (2006.01) |
| *A61K 47/28* | (2006.01) |
| *A61K 47/32* | (2006.01) |

(52) U.S. Cl.
CPC .......... *A61K 9/1623* (2013.01); *A61K 9/0019* (2013.01); *A61K 9/10* (2013.01); *A61K 9/145* (2013.01); *A61K 9/146* (2013.01); *A61K 9/1617* (2013.01); *A61K 9/1635* (2013.01); *A61K 9/1688* (2013.01); *A61K 31/5415* (2013.01); *A61K 47/02* (2013.01); *A61K 47/10* (2013.01); *A61K 47/26* (2013.01); *A61K 47/28* (2013.01); *A61K 47/32* (2013.01)

(58) Field of Classification Search
None
See application file for complete search history.

(56) References Cited

U.S. PATENT DOCUMENTS

| | | |
|---|---|---|
| 4,783,484 A | 11/1988 | Violante et al. |
| 4,826,689 A | 5/1989 | Violanto et al. |
| 4,997,454 A | 3/1991 | Violante et al. |
| 5,118,528 A | 6/1992 | Fessi et al. |
| 5,145,684 A | 9/1992 | Liversidge et al. |
| 5,298,262 A | 3/1994 | Na et al. |
| 5,302,401 A | 4/1994 | Liversidge et al. |
| 5,318,767 A | 6/1994 | Liversidge et al. |
| 5,326,552 A | 7/1994 | Na et al. |
| 5,328,404 A | 7/1994 | Bacon |
| 5,336,507 A | 8/1994 | Na et al. |
| 5,340,564 A | 8/1994 | Illig et al. |
| 5,346,702 A | 9/1994 | Na et al. |
| 5,349,957 A | 9/1994 | Yudelson |
| 5,352,459 A | 10/1994 | Hollister et al. |
| 5,399,363 A | 3/1995 | Liversidge et al. |
| 5,401,492 A | 3/1995 | Kellar et al. |
| 5,429,824 A | 7/1995 | June |
| 5,447,710 A | 9/1995 | Na et al. |
| 5,451,393 A | 9/1995 | Liversidge et al. |
| 5,466,440 A | 11/1995 | Ruddy et al. |
| 5,470,583 A | 11/1995 | Na et al. |
| 5,472,683 A | 12/1995 | Illig |
| 5,494,683 A | 2/1996 | Liversidge et al. |
| 5,500,204 A | 3/1996 | Osifo |
| 5,510,118 A | 4/1996 | Bosch et al. |
| 5,518,187 A | 5/1996 | Bruno et al. |
| 5,518,738 A | 5/1996 | Eickhoff et al. |
| 5,521,218 A | 5/1996 | Osifo |
| 5,525,328 A | 6/1996 | Bacon et al. |
| 5,534,270 A | 7/1996 | De Castro |

(Continued)

FOREIGN PATENT DOCUMENTS

| | | |
|---|---|---|
| EP | 0 275 796 | 7/1988 |
| EP | 0 499 299 A2 | 8/1992 |

(Continued)

OTHER PUBLICATIONS

Office Action issued in related Japanese Patent Application No. 2012-513185, dated Apr. 12, 2016.

(Continued)

*Primary Examiner* — Robert A Wax
*Assistant Examiner* — Quanglong N Truong
(74) *Attorney, Agent, or Firm* — Foley & Lardner LLP

(57) ABSTRACT

This invention is directed to reduction of flake-like aggregation in nanoparticulate compositions. Also encompassed by the invention are compositions comprising a nanoparticulate active agent, at least one surface stabilizer and a flake-like aggregation reducing agent, such as a buffer and a sugar. The nanoparticulate active agent compositions comprise particles of the active agent having an effective average particle size of less than about 2000 nm.

15 Claims, 6 Drawing Sheets

(56) References Cited

U.S. PATENT DOCUMENTS

| | | |
|---|---|---|
| 5,543,133 A | 8/1996 | Swanson et al. |
| 5,552,160 A | 9/1996 | Liversidge et al. |
| 5,560,931 A | 10/1996 | Eickhoff et al. |
| 5,560,932 A | 10/1996 | Bagchi et al. |
| 5,565,188 A | 10/1996 | Wong et al. |
| 5,569,448 A | 10/1996 | Wong et al. |
| 5,571,536 A | 11/1996 | Eickhoff et al. |
| 5,573,749 A | 11/1996 | Illig |
| 5,573,750 A | 11/1996 | Singh |
| 5,573,783 A | 11/1996 | Desieno et al. |
| 5,580,579 A | 12/1996 | Ruddy et al. |
| 5,585,108 A | 12/1996 | Ruddy et al. |
| 5,587,143 A | 12/1996 | Wong |
| 5,591,456 A | 1/1997 | Franson et al. |
| 5,593,657 A | 1/1997 | Ruddy et al. |
| 5,622,938 A | 4/1997 | Wong |
| 5,628,981 A | 5/1997 | Liversidge et al. |
| 5,643,552 A | 7/1997 | Illig |
| 5,662,883 A | 9/1997 | Bagchi et al. |
| 5,665,331 A | 9/1997 | Bagchi et al. |
| 5,718,388 A | 2/1998 | Czekai et al. |
| 5,718,919 A | 2/1998 | Ruddy et al. |
| 5,741,522 A | 4/1998 | Violante et al. |
| 5,747,001 A | 5/1998 | Wiedmann et al. |
| 5,776,496 A | 7/1998 | Violante et al. |
| 5,834,025 A | 11/1998 | De Garavilla et al. |
| 5,862,999 A | 1/1999 | Czekai et al. |
| 6,045,829 A | 4/2000 | Liversidge et al. |
| 6,068,858 A | 5/2000 | Liversidge et al. |
| 6,153,225 A | 11/2000 | Lee et al. |
| 6,165,506 A | 12/2000 | Jain et al. |
| 6,207,178 B1 | 3/2001 | Westesen |
| 6,221,400 B1 | 4/2001 | Liversidge et al. |
| 6,264,922 B1 | 7/2001 | Wood et al. |
| 6,267,989 B1 | 7/2001 | Liversidge et al. |
| 6,270,806 B1 | 8/2001 | Liversidge et al. |
| 6,316,029 B1 | 11/2001 | Jain et al. |
| 6,375,986 B1 | 4/2002 | Ryde et al. |
| 6,406,718 B1 | 6/2002 | Cooper |
| 6,428,814 B1 | 8/2002 | Bosch |
| 6,431,478 B1 | 8/2002 | Reed et al. |
| 6,432,381 B2 | 8/2002 | Liversidge et al. |
| 6,582,285 B2 | 6/2003 | Czekai et al. |
| 6,592,903 B2 | 7/2003 | Ryde et al. |
| 6,656,504 B1 | 12/2003 | Bosch et al. |
| 6,742,734 B2 | 6/2004 | Reed et al. |
| 6,745,962 B2 | 6/2004 | Reed et al. |
| 6,908,626 B2 | 6/2005 | Cooper et al. |
| 6,969,529 B2 | 11/2005 | Bosch et al. |
| 6,976,647 B2 | 12/2005 | Reed et al. |
| 6,991,191 B2 | 1/2006 | Reed et al. |
| 7,101,576 B2 | 9/2006 | Hovey et al. |
| 7,198,792 B2 | 4/2007 | Cooper et al. |
| 7,244,451 B2 | 7/2007 | Bosch et al. |
| 7,276,249 B2 | 10/2007 | Ryde et al. |
| 7,288,267 B2 | 10/2007 | Bosch et al. |
| 7,320,802 B2 | 1/2008 | Ryde et al. |
| 7,390,505 B2 | 6/2008 | Gustow et al. |
| 2001/0053664 A1 | 12/2001 | Czekai et al. |
| 2002/0012675 A1 | 1/2002 | Jain et al. |
| 2002/0179758 A1 | 12/2002 | Reed et al. |
| 2003/0023203 A1 | 1/2003 | Lavi et al. |
| 2003/0087308 A1 | 5/2003 | Lindner et al. |
| 2003/0095928 A1 | 5/2003 | McGurk et al. |
| 2003/0108616 A1 | 6/2003 | Bosch et al. |
| 2003/0119825 A1 | 6/2003 | Folger et al. |
| 2003/0137067 A1 | 7/2003 | Cooper et al. |
| 2003/0181411 A1 | 9/2003 | Bosch et al. |
| 2003/0185869 A1 | 10/2003 | Wertz et al. |
| 2003/0215502 A1 | 11/2003 | Pruss et al. |
| 2003/0232796 A1 | 12/2003 | Cooper et al. |
| 2004/0015134 A1 | 1/2004 | Lavi et al. |
| 2004/0018242 A1 | 1/2004 | Cunningham et al. |
| 2004/0033202 A1 | 2/2004 | Cooper et al. |
| 2004/0033267 A1 | 2/2004 | Merisko-Liversidge et al. |
| 2004/0057905 A1 | 3/2004 | Wood et al. |
| 2004/0101566 A1 | 5/2004 | Cooper et al. |
| 2004/0105778 A1 | 6/2004 | Lee et al. |
| 2004/0105889 A1 | 6/2004 | Ryde et al. |
| 2004/0115134 A1 | 6/2004 | Merisko-Liversidge |
| 2004/0141925 A1 | 7/2004 | Bosch et al. |
| 2004/0156872 A1 | 8/2004 | Bosch et al. |
| 2004/0156895 A1 | 8/2004 | Pruitt et al. |
| 2004/0173696 A1 | 9/2004 | Cunningham et al. |
| 2004/0195413 A1 | 10/2004 | Reed et al. |
| 2004/0208833 A1 | 10/2004 | Hovey et al. |
| 2004/0229038 A1 | 11/2004 | Cooper et al. |
| 2004/0258757 A1 | 12/2004 | Bosch et al. |
| 2004/0258758 A1 | 12/2004 | Gustow et al. |
| 2005/0004049 A1 | 1/2005 | Liversidge |
| 2005/0019412 A1 | 1/2005 | Bosch et al. |
| 2005/0031691 A1 | 2/2005 | McGurk et al. |
| 2005/0042177 A1 | 2/2005 | Ryde et al. |
| 2005/0063913 A1 | 3/2005 | Pruitt et al. |
| 2005/0147664 A1 | 7/2005 | Liversidge et al. |
| 2005/0233001 A1 | 10/2005 | Hovey et al. |
| 2005/0238725 A1 | 10/2005 | Cunningham et al. |
| 2005/0276974 A1 | 12/2005 | Ryde et al. |
| 2006/0079516 A1 | 4/2006 | Henke et al. |
| 2006/0121112 A1 | 6/2006 | Jenkins et al. |
| 2006/0154918 A1 | 7/2006 | Liversidge et al. |
| 2006/0159628 A1 | 7/2006 | Liversidge et al. |
| 2006/0159766 A1 | 7/2006 | Jenkins et al. |
| 2006/0159767 A1 | 7/2006 | Jenkins et al. |
| 2006/0165806 A1 | 7/2006 | Liversidge et al. |
| 2006/0188566 A1 | 8/2006 | Liversidge et al. |
| 2006/0193920 A1 | 8/2006 | Bosch et al. |
| 2006/0198896 A1 | 9/2006 | Liversidge et al. |
| 2006/0204588 A1 | 9/2006 | Liversidge et al. |
| 2006/0210638 A1 | 9/2006 | Liversidge et al. |
| 2006/0210639 A1 | 9/2006 | Liversidge et al. |
| 2006/0216353 A1 | 9/2006 | Liversidge et al. |
| 2006/0246141 A1 | 11/2006 | Liversidge et al. |
| 2006/0246142 A1 | 11/2006 | Liversidge et al. |
| 2006/0275372 A1 | 12/2006 | Jenkins et al. |
| 2006/0292214 A1 | 12/2006 | Jenkins et al. |
| 2007/0003615 A1 | 1/2007 | Jenkins et al. |
| 2007/0003628 A1 | 1/2007 | Liversidge et al. |
| 2007/0015719 A1 | 1/2007 | Jenkins et al. |
| 2007/0042049 A1 | 2/2007 | Liversidge et al. |
| 2007/0048378 A1 | 3/2007 | Swanson et al. |
| 2007/0059371 A1 | 3/2007 | Liversidge et al. |
| 2007/0065374 A1 | 3/2007 | Liversidge et al. |
| 2007/0098805 A1 | 5/2007 | Liversidge et al. |
| 2007/0104792 A1 | 5/2007 | Jenkins |
| 2007/0110776 A1 | 5/2007 | Cooper et al. |
| 2007/0122486 A1 | 5/2007 | McGurk et al. |
| 2007/0134339 A1 | 6/2007 | Jenkins et al. |
| 2007/0141159 A1 | 6/2007 | Bosch et al. |
| 2007/0148100 A1 | 6/2007 | Jenkins |
| 2007/0160675 A1 | 7/2007 | Devane et al. |
| 2007/0178051 A1 | 8/2007 | Pruitt et al. |
| 2007/0202180 A1 | 8/2007 | Liversidge et al. |
| 2007/0224279 A1 | 9/2007 | Liversidge et al. |
| 2007/0264348 A1 | 11/2007 | Ryde et al. |
| 2007/0281011 A1 | 12/2007 | Jenkins et al. |
| 2007/0298098 A1 | 12/2007 | Jenkins et al. |
| 2007/0298115 A1 | 12/2007 | Ryde et al. |
| 2008/0003295 A1 | 1/2008 | Bosch et al. |
| 2008/0025807 A1 | 1/2008 | Reed et al. |
| 2008/0050461 A1 | 2/2008 | Merisko-Liversidge et al. |
| 2008/0095851 A1 | 4/2008 | Ryde et al. |
| 2008/0102121 A1 | 5/2008 | Devane et al. |
| 2008/0107741 A1 | 5/2008 | Merisko-Liversidge et al. |
| 2008/0113025 A1 | 5/2008 | Devane et al. |
| 2008/0124389 A1 | 5/2008 | Jenkins et al. |
| 2008/0124393 A1 | 5/2008 | Swanson et al. |
| 2008/0132493 A1 | 6/2008 | Folger et al. |
| 2008/0138424 A1 | 6/2008 | Ryde et al. |
| 2008/0152585 A1 | 6/2008 | Ryde et al. |
| 2008/0152720 A1 | 6/2008 | Jenkins et al. |
| 2008/0193520 A1 | 8/2008 | Moschwitzer et al. |
| 2008/0214538 A1 | 9/2008 | Bourrie et al. |

(56) References Cited

U.S. PATENT DOCUMENTS

| | | | |
|---|---|---|---|
| 2010/0137292 | A1 | 6/2010 | Turp et al. |
| 2010/0316725 | A1 | 12/2010 | Ryde et al. |
| 2012/0141548 | A1 | 6/2012 | Dodd et al. |

FOREIGN PATENT DOCUMENTS

| | | |
|---|---|---|
| JP | 2008-538552 | 10/2008 |
| JP | 2012-528171 | 11/2012 |
| WO | WO 94/20072 | 9/1994 |
| WO | WO 97/14407 | 4/1997 |
| WO | WO 2004/006959 A1 | 1/2004 |
| WO | WO 2005/007133 A1 | 1/2005 |
| WO | WO 2005/049078 A2 | 6/2005 |
| WO | WO 2005/105101 A1 | 11/2005 |
| WO | WO 2006/000306 A1 | 1/2006 |
| WO | WO 2006/088894 A2 | 8/2006 |
| WO | WO 2007/036809 | 4/2007 |
| WO | WO 2007/135362 A2 | 11/2007 |
| WO | WO 2007/150075 | 12/2007 |
| WO | WO 2007/1500075 A2 | 12/2007 |
| WO | WO 2008/008733 A2 | 1/2008 |
| WO | WO 2008/079290 A2 | 7/2008 |
| WO | WO 2008/118754 A2 | 10/2008 |
| WO | WO 2009/098469 A1 | 8/2009 |

OTHER PUBLICATIONS

Ahmed et al., "Meloxicam in rheumatoid arthritis," pp. 739-751 (2005).
Altman et al., "Efficacy Assessment of Meloxicam, a Preferential Cyclooxygenaise-2 Inhibitor, in Acute Coronary Syndromes without ST-Segment Elevation," 191-195 (2002).
Aoki et al., "Premedication with cyclooxygenase-2 inhibitor meloxicam reduced postoperative pain in patients after oral surgery," pp. 613-617 (2006).
Auvinet et al., "Comparison of the Onset and Intensity of Action of Intramuscular Meloxicam Oral Meloxicam in Patients with Acute Sciatica," *Clin. Therap.*, vol. 17, No. 6, pp. 1078-1090 (1995).
Barner, "Review of Clinical Trials and Benefit/Risk Ratio of Meloxicam," pp. 29-37 (1996).
Bosch et al., "Efficacy and Tolerability of Intramuscular and Oral Meloxicam in Patents with Acute Lumbago: A Comparison with Intramuscular and Oral Piroxicam," pp. 29-38 (1997).
Busch et al., "Pharmacokinetics of Meloxicam in Animals and the Relevance to Humans," *Drug Metabolism and Disposition*, vol. 26, No. 6, pp. 576-584 (1998).
Busch et al., "The effect of cholestyramine on the pharmacokinetics of meloxicam, a new non-steroidal anti-inflammatory drug (NSAID), in man," pp. 269-272 (1995).
Calvo et al., "Analgesic and anti-inflammatory dose-response relationship of 7.5 and 15 mg meloxicam after lower third molar removal: a double-blind, randomized, crossover study," *Int. J. Oral Maxillofac. Sur.*, vol. 36, pp. 26-31 (2007).
Chen et al., "Cyclooxygenase-2 selective non-steroidal anti-inflammatory drugs (etodalac, meloxicam, celecoxib, rofecoxib, etoricoxib, valdecoxib and lumiracoxib) for osteoarthritis and rheumatoid arthritis: a systematic review and economic evaluation," vol. 12, No. 11, 4 pgs. (2008).
Chung, "The Use of Injectable Nonsteroidal Anti-Inflammatory Drugs in Local Accident & Emergency Practice," *Hong King Journ. of Emerg. Med.*, pp. 65-71 (2002).
Colberg et al., "The efficacy and tolerability of an 8-day administration of intravenous and oral meloxicam: a comparison with intramuscular and oral diclofenac in patients with acute lumbago," *Current Medical Research and Opin.*, vol. 13, No. 7, pp. 363-377 (1996).
Combe et al., "Comparison of Intramuscular and Oral Meloxicam in Rheumatoid Arthritis Patients," pp. 10-16 (2001).
Davies et al., "Clinical Pharmacokinetics of Meloxicam," pp. 115-126 (1999).

DeAndrade et al, "Ketorolec Versus Meperidine for Pain Relief After Orthopaedic Surgery," pp. 302-312 (1996).
Degner et al., "Pharmacological, Pharmacokinetic and Clinical Profile of Meloxicam," *Drugs of Today*, vol. 33, No. 10, pp. 739-758 (1997).
Del Tacca et al., "Efficacy and Tolerability of Meloxicam, a COX-2 Preferential Nonsteroidal Anti-Inflammatory Drug," *Clin. Drug. Invest.*, vol. 22, No. 12, pp. 799-818 (2002).
Engelhardt, "Meloxicam Inhibits Preferentially COX-2," *Euro. Journ. of Pharm.*, Abstracts of 4th Annual Meeting of the German Socieity of Clin. Pharmacology and Therpay, 2 pgs. (1994).
Engelhardt et al., "Anti-inflammatory, analgesic, antipyretic and related properties of meloxicam, a new non-steroidal anti-inflammatory agent with favourable gastrointestinal tolerance," *Inflamm. Res.*, vol. 44, pp. 423-433 (1995).
Euller-Ziegler et al., "Meloxicam: a review of its pharmacokinetics, efficacy and tolerability following intramuscular administration," pp. 5-9 (2001).
Filatova et al., "Efficacy of movalis in the treatment of acute low back pains," pp. 33-37 (2005). [English Abstract].
Furst, "Meloxicam: Selective COX-2 Inhibition in Clinical Practice," pp. 21-27 (1997).
Gates et al., "Meloxicam: a reappraisal of Pharmacokinetics, efficacy and safety," pp. 2117-2140 (2005).
Gebuhr et al., "A Multiple-dose, Double-blind Comparison of Intramuscularly and Orally Administered Ketorolac Tromethamine and Ketogan® in Patients with Pain Following Orthopaedic Surgery," pp. 202-217 (1994).
Ghozlan et al., "Tolerability of Multiple Administration of Intramuscular Meloxicam: A comparison with Intramuscular Piroxicam in patients with rheumatoid arthritis or osteoarthritis," pp. 51-55 (1996).
Gillis et al., "Ketorolac: A Reappraisal of its Pharmacodynamic and Pharmacokinetic Properties and Therapeutic Use in Pain Management," Drugs, vol. 53, No. 1, pp. 139-188 (1997).
Haas et al., "An Update on Analgesics for the Management of Acute Postoperative Dental Pain," *Journ. of the Canadian Dental Assoc.*, vol. 68, No. 8, pp. 476-482 (2002).
Hawkey et al., "Gastrointestinal Tolerability of Meloxicam Compared to Diclofenac in Osteoarthritis Patients," *British Society for Rheumatology*, pp. 937-945 (1998).
Hill et al., "Analgesic Efficacy of the Cyclooxygenase-Inhibiting Nitric Oxide Donor AZD3582 in Postoperative Dental Pain: Comparison with Naproxen and Rofecoxib in Two Randomized, Double-Blind, Placebo-Controlled Studies," *Clinical Therapeutics*, vol. 28, No. 9, pp. 1279-1295 (2006).
Hinz et al., "Can Drug Removals Involving Cyclooxygenase-2 Inhibitors be Avoided? A Plea for Human Pharmacology," *Trends in Pharmacological Sciences*, pp. 391-397 (2008).
Hosein et al., "Evaluation of Meloxicam (a COX-2 Inhibitor) for Management of Postoperative Endodontic Pain: A Double-blind Placebo-controlled Study," *Journ. of Encodontics*, pp. 634-637 (2003)
Issioui et al., "The Efficacy of Premedication with Celecoxib and Acetaminophen in Preventing Pain After Otolaryngologic Surgery," *Anesh. Analog.*, pp. 1188-1193 (2002).
Jick, "The Risk of Gastrointestinal Bleed, Myocardial Infarction and Newly Diagnosed Hypertension in Users of Meloxicam, Diclofenac, Naproxen, and Piroxicam," *Pharmacotherapy*, vol. 20, No. 7, pp. 741-744 (2000).
Kurukahvecioglu et al., "Effect of Meloxicam on Postoperative Pain Relief after Inguinal Hernia Repair with Local Anaesthesia," *West Indian Med. J.*, vol. 56, No. 6, pp. 530-533 (2007).
Lugar et al., Structure and physicochemical properties of meloxicam, a new NSAID, pp. 175-187 (1996).
Malan et al., "The Cyclooxygenase-2 Specific Inhibitor Parecoxib Sodium is as Effective as 12 mg of Morphone Administered Intramuscularly for Treating Pain After Gynecologic Laparotomy Surgery," *Anesth Analg.*, 454-460 (2005).
Mazurov et al., "Use of meloxicam (movalis) in patients with rheumatic diseases with concomitant coronary heart disease," *Klin Med (Mosk)*, vol. 82, No. 12, pp. 54-59 (2004). [English Abstract].

(56) References Cited

OTHER PUBLICATIONS

Mitchell et al., Clinico-pharmacological studies on Ketoprofen ('Orudis'), pp. 423-430 (1975).
Naidu et al., "Physicochemical characterization and dissolution properties of meloxicam-cyclodextrin binary systems," pp. 75-86 (2004).
Narjes et al., "Pharmacokinetics and tolerability of meloxicam after i.m. administration," *Br. J. Clin. Pharm.*, vol. 41, pp. 135-139 (1996).
Narjes et al., "Parenteral Tolerability of Meloxicam in Healthy Volunteers," p. 61 [P87].
Nekoofar et al., "Evaluation of Meloxicam (a COX-2 Inhibitor) for Management of Postoperative Endodontic Pain: A Double-blind Placebo-controlled Study," *Journ. of Endodontics*, vol. 29, No. 10, pp. 634-637 (2003).
Nikanne et al., "Comparison of perioperative ketoprofen 2.0 mg kg-1 with 0.5 mg kg-1 i.v. In small children during adenoidectomy," *British Journ. of Anaesthesia*, vol. 79, pp. 606-608 (1997).
Odinak et al., "Use of Movalis in Treatment of Dorsophathy," 29-32 (2004). [English Abstract Included].
Palangio et al., "Combination Hydrocodone and Ibuprofen Versus Combination Oxycodone and Acetaminophen in the Treatment of Postoperative Obstetric or Gynecologic Pain," *Clin. Therapeutics*, vol. 22, No. 5, pp. 600-612 (2000).
Pallapies et al., "Effects on Platelet Functions and Pharmacokinetics of Azapropazone and Ketorolac Tromethamine Given as Single Parenteral Doses," pp. 335-339 (1993).
Panara et al., Dose-Dependent Inhibition of Platelet Cyclooxygenase-1 and Monocyte Cyclooxygenase-2 by Meloxicam in Healthy Subjects, pp. 276-280 (1999).
Power et al., "Comparison of I.M. Ketorolac Trometamol and Morphine Sulphate for Pain Relief after Cholecystectomy," *British Journ. of Anaesthesia*, vol. 65, pp. 448-455 (1990).
Rani et al., "Determination of Oral Meloxicam Pharmacokinetic Parameters in Asian Indians: Comparison with a German Population," *Saudi Pharm. J.*, vol. 12, No. 4, pp. 144-149 (2004).
Rao et al., "Evolution of Nonsteroidal Anti-Inflammatory Drugs (NSAIDs): Cyclooxygenase (COX) Inhibition and Beyond," *J. Pharm. Pharmaceuit Sci.*, pp. 81-110 (2008).
Rinder et al., "Effects of Meloxicam on Platelet Function in Healthy Adults: A Randomized, Double-Blind, Placebo-Controlled Trial," *J. Clin. Pharmacol.*, vol. 42, pp. 881-886 (2002).
Romsing et al., "Postoperative Analgesia is not Different After Local vs Systemic administration of Meloxicam in Patients Undergoing Inguinal Hernia Repair," *Can. J. Anesth.*, vol. 48, No. 10, pp. 978-984 (2001).
Schmid et al., "Pharmacokinetics and Metabolic Pattern after Intravenous Infusion and Oral Administration to Healthy Subjects," pp. 1206-1213 (1995).
Singh et al., "Risk of Serious Upper Gastrointestinal and Cardiovascular Thromboembolic Complications with Meloxicam," pp. 100-106 (2004).
Stei et al., Local Tissue Tolerability of Meloxicam, a New NSAID: Indications for Parenteral, Dermal and Mucosal Administration, *British Journ. of Rheumatology*, vol. 35 (Suppl. 1), pp. 44-50 (1996).
Strand, Are COX-2 Inhibitors Preferable to Non-Selective Non-Steroidal Anti-Inflammatory Drugs in Patients with Risk of Cardiovascular Events Taking Low-Dose Aspirin?, Lancet, pp. 2138-2151 (2007).
Sunshine et al., "Analgesic Efficacy of a Hydrocodone with Ibuprofen Combination Compared with Ibuprofen Alone for the Treatment of Acute Postoperative Pain," *J. Clin. Pharmacol.*, vol. 37, pp. 908-915 (1997).
Swamy et al., "Orodispersible Tablets of Meloxicam using Disintegrant Blends for Improved Efficacy," *Indian Journ. of Pharm. Sci.*, pp. 836-841 (2007).
Thompson et al., "Effect of Meloxicam on Postoperative Pain After Abdominal Hysterectomy," *British Journ. of Anaesth.*, vol. 84, No. 2, pp. 151-154 (2000).
Thwaites et al., "Intravenous Ketorolac Tromethamine Does not Worsen Platelet Function During Knee Arthroscopy Under General Anesthesia," *Anesth. Analg.*, vol. 81, pp. 119-124 (1995).
Thwaites et al., "Intravenous Ketorolac Tromethamine Worsens Platelet Function During Knee Arthroscopy Under Spinal Anesthesia," *Anesth. Analg.*, vol. 82, pp. 1176-1181 (1996).
Turck et al., Clinical Pharmacokinetics of Meloxicam, *Arzneim.-Forsch./Drug Res.*, vol. 47(1), pp. 253-258 (1997).
Van Hecken et al., "Comparative Inhibitory Activity of Rofecoxib, Meloxicam, Diclofenac, Ibuprofen, and Naproxen on COX-2 versus COX-1 in Healthy Volunteers," *J. Clin. Pharm.*, vol. 40, pp. 1109-1120 (2000).
Van Kraaij et al., "A comparison of the effects of nabumetone vs. meloxicam on serum thromboxane $B_2$ and platelet function in healthy volunteers," pp. 644-647 (2002).
Weber et al., "COX 2 selectivity of non-steroidal anti-inflammatory drugs and perioperative blood loss in hip surgery. A randomized comparison of indeomethacin and meloxicam," pp. 963-966 (2003).
Wideman et al., "Analgesic Efficacy of a combination of hydrocodone with ibuprofen in postoperative pain," pp. 66-76 (1999).
Zelenakas et al., "Analgesic efficacy of single oral doses of lumiracoxib and ibuprofen in patients with postoperative dental pain," *J. Clin. Pract.*, vol. 58, No. 3, pp. 251-256 (2004).
Gravestock, Analytical Service Report, Meloxicam pKa and Solubility Analysis, 7 pgs., (2008).
Gravestock, Meloxicam Aq GI-Dissolution, 3 pgs. (2008).
Dreiser et al., Oral meloxicam is effective in acute sciatica: two randomised, double-blind trials versus placebo or diclofenac, *Inflamm Res.*, vol. 50, Suppl 1, pp. S17-23 (2001).
Akarsu et al., "Preemptive meloxicam for postoperative pain relief after abdominal hysterectomy," *Clin Exp Obstet Gynecol.*, vol. 31, No. 2, pp. 133-136 (2004).
De Mello e tal., "Double-blind study to evaluate efficacy and safety of meloxicam 7.5 mg and 15 mg versus mefenamic acid 1500 mg in the treatment of primary dysmenorrheal," *Acta Obstet Gynecol Scand.*, vol. 83, No. 7, pp. 667-673 (2004).
Cheng et al., "A single-blind, randomized, controlled trial to assess the efficacy and tolerability of rofecoxib, diclofenac sodium, and meloxicam in patients with acute gouty arthritis," *Clin Ther.*, vol. 26, No. 3, pp. 399-406 (2004).
Carroll et al., "Analgesic efficacy of preoperative administration of meloxicam or butorphanol in onychectomized cats," *J. Am. Vet. Med. Assoc.*, vol. 226, No. 6, pp. 913-9 (2005).
Deneuche et al., "Analgesic comparison of meloxicam or ketoprofen for orthopedic surgery in dogs," *Vet Surg.*, vol. 33, No. 6, pp. 650-660 (2004).
Fowler et al, An evaluation of the analgesic effects of meloxicam in addition to epidural morphine/mepivacaine in dogs undergoing cranial cruciate ligament repair, *Can. Vet. J.*, vol. 44, No. 8, pp. 643-648 (2003).
Caulkett et al., A comparison of the analgesic effects of butorphanol with those of meloxicam after elective ovariohysterectomy in dogs, *Can. Vet J.*, vol. 44, No. 7, pp. 565-570 (2003).
Budsberg et al., "Evaluation of intravenous administration of meloxicam for perioperative pain management following stifle joint surgery in dogs," *Am J Vet Res.*, vol. 63, No. 11, pp. 1557-1563 (2002).
Lascelles et al., "Evaluation of the clinical efficacy of meloxicam in cats with painful locomotor disorders," *J Small Anim Pract.*, vol. 42, No. 12, pp. 587-593 (2001).
Mathews et al., "Safety and efficacy of preoperative administration of meloxicam, compared with that of ketoprofen and butorphanol in dogs undergoing abdominal surgery," *Am J Vet Res.*, vol. 62, No. 6, pp. 882-888 (2001).
Scientific Discussion, EMEA, 1-96 (2007).
International Search Report for related International Patent Application No. PCT/US2010/036304, completed Sep. 10, 2010.
Written Opinion for related International Patent Application No. PCT/US2010/036304, completed Sep. 10, 2010.
Hintz et al., "The Effect of Particle Size distribution on Dissolution Rate and Oral Absorption," *Intern. Journ. of Pharm.*, vol. 51, pp. 9-17 (1989).

(56) References Cited

OTHER PUBLICATIONS

*Handbook of Pharmaceutical Excipients*, published jointly by the American Pharmaceutical Association and The Pharmaceutical Society of Great Britain (The Pharmaceutical Press, 5$^{th}$ ed., 2005). [Book].
J. Cross and E. Singer, *Cationic Surfactants: Analytical and Biological Evaluation* (Marcel Dekker, 1994). [Book].
P. and D. Rubingh (Editor), *Cationic Surfactants: Physical Chemistry* (Marcel Dekker, 1991). [Book].
J. Richmond, *Cationic Surfactants: Organic Chemistry*, (Marcel Dekker, 1990). [Book].
Kocbek et al., "Preparation and Evaluation of Nanosuspensions for Enhancing the Dissolution of Poorly Soluble Drugs," International Journ. of Pharmaceutics, *Pharmaceutical Nanotechnology*, pp. 179-186 (2006).
International Search Report cited in related International Patent Application No. PCT/US2010/036127, dated Aug. 18, 2011.
European Office Action issued in related European Patent Application No. 10728470.5, dated Feb. 20, 2013.
Lucrin Depot—1 Month Injection Consumer Medicine Information Oct. 2004, pp. 1-5.
Notice of Reasons for Rejection cited in related Japanese Patent Application No. 2012-513185, dated May 20, 2014.
Chowdary et al., "Enhancement of Dissolution Rate of Meloxicam," *Indian Journ. of Pharm. Sci.*, vol. 63, No. 2, pp. 150-154 (2001).
European Office Action issued in related European Patent Application No. 10 728 470.5, dated Sep. 30, 2014.
Notice of Reasons for Rejection issued in related Japanese Patent Application No. 2015-185009, dated May 23, 2017.
Non-Final Office Action issued in related U.S. Appl. No. 15/130,255, dated Mar. 9, 2017.
Non-Final Office Action issued in related U.S. Appl. No. 15/130,331, dated Mar. 10, 2017.
Non-Final Office Action issued in related U.S. Appl. No. 15/130,255, dated Sep. 21, 2017.
Non-Final Office Action issued in related U.S. Appl. No. 15/130,331, dated Sep. 21, 2017.
Notice of Allowance issued in related U.S. Appl. No. 15/130,255, dated Jan. 25, 2018.
Notice of Allowance issued in related U.S. Appl. No. 15/130,331, dated Jan. 25, 2018.

% Growth Over 3 Months for 0.5% PVP

% Growth Over 3 Months of 0.75% PVP

REDUCTION OF FLAKE-LIKE AGGREGATION IN NANOPARTICULATE ACTIVE AGENT COMPOSITIONS

CROSS REFERENCE TO RELATED APPLICATIONS

This application is a continuation of U.S. patent application Ser. No. 14/133,191, filed Dec. 18, 2013, now U.S. Pat. No. 9,345,665, which is a divisional of U.S. patent application Ser. No. 12/788,196, filed May 26, 2010, now abandoned, which claims priority from U.S. Provisional Patent Application No. 61/181,641, filed May 27, 2009. The contents of these applications are incorporated herein by reference in their entirety.

FIELD OF THE INVENTION

The present invention relates generally to reduction of flake-like aggregation in nanoparticulate active agent compositions. More specifically, the invention relates to compositions comprising a nanoparticulate active agent, at least one surface stabilizer and a flake-like aggregation reducing agent. The nanoparticulate active agent compositions comprise particles of an active agent having an effective average particle size of less than about 2000 nm.

BACKGROUND OF THE INVENTION

A. Background Regarding Nanoparticulate Active Agent Compositions

Nanoparticulate active agent compositions, first described in U.S. Pat. No. 5,145,684 ("the '684 patent"), are particles comprising a poorly soluble therapeutic or diagnostic agent having adsorbed onto or associated with the surface thereof a non-crosslinked surface stabilizer.

Methods of making nanoparticulate active agent compositions are described in, for example, U.S. Pat. Nos. 5,518,187 and 5,862,999, both for "Method of Grinding Pharmaceutical Substances;" U.S. Pat. No. 5,718,388, for "Continuous Method of Grinding Pharmaceutical Substances;" and U.S. Pat. No. 5,510,118 for "Process of Preparing Therapeutic Compositions Containing Nanoparticles."

Nanoparticulate active agent compositions are also described, for example, in U.S. Pat. No. 5,298,262 for "Use of Ionic Cloud Point Modifiers to Prevent Particle Aggregation During Sterilization;" U.S. Pat. No. 5,302,401 for "Method to Reduce Particle Size Growth During Lyophilization;" U.S. Pat. No. 5,318,767 for "X-Ray Contrast Compositions Useful in Medical Imaging;" U.S. Pat. No. 5,326,552 for "Novel Formulation For Nanoparticulate X-Ray Blood Pool Contrast Agents Using High Molecular Weight Non-ionic Surfactants;" U.S. Pat. No. 5,328,404 for "Method of X-Ray Imaging Using Iodinated Aromatic Propanedioates;" U.S. Pat. No. 5,336,507 for "Use of Charged Phospholipids to Reduce Nanoparticle Aggregation;" U.S. Pat. No. 5,340,564 for "Formulations Comprising Olin 10-G to Prevent Particle Aggregation and Increase Stability;" U.S. Pat. No. 5,346,702 for "Use of Non-Ionic Cloud Point Modifiers to Minimize Nanoparticulate Aggregation During Sterilization;" U.S. Pat. No. 5,349,957 for "Preparation and Magnetic Properties of Very Small Magnetic-Dextran Particles;" U.S. Pat. No. 5,352,459 for "Use of Purified Surface Modifiers to Prevent Particle Aggregation During Sterilization;" U.S. Pat. Nos. 5,399,363 and 5,494,683, both for "Surface Modified Anticancer Nanoparticles;" U.S. Pat. No. 5,401,492 for "Water Insoluble Non-Magnetic Manganese Particles as Magnetic Resonance Enhancement Agents;" U.S. Pat. No. 5,429,824 for "Use of Tyloxapol as a Nanoparticulate Stabilizer;" U.S. Pat. No. 5,447,710 for "Method for Making Nanoparticulate X-Ray Blood Pool Contrast Agents Using High Molecular Weight Non-ionic Surfactants;" U.S. Pat. No. 5,451,393 for "X-Ray Contrast Compositions Useful in Medical Imaging;" U.S. Pat. No. 5,466,440 for "Formulations of Oral Gastrointestinal Diagnostic X-Ray Contrast Agents in Combination with Pharmaceutically Acceptable Clays;" U.S. Pat. No. 5,470,583 for "Method of Preparing Nanoparticle Compositions Containing Charged Phospholipids to Reduce Aggregation;" U.S. Pat. No. 5,472,683 for "Nanoparticulate Diagnostic Mixed Carbamic Anhydrides as X-Ray Contrast Agents for Blood Pool and Lymphatic System Imaging;" U.S. Pat. No. 5,500,204 for "Nanoparticulate Diagnostic Dimers as X-Ray Contrast Agents for Blood Pool and Lymphatic System Imaging;" U.S. Pat. No. 5,518,738 for "Nanoparticulate NSAID Formulations;" U.S. Pat. No. 5,521,218 for "Nanoparticulate Iododipamide Derivatives for Use as X-Ray Contrast Agents;" U.S. Pat. No. 5,525,328 for "Nanoparticulate Diagnostic Diatrizoxy Ester X-Ray Contrast Agents for Blood Pool and Lymphatic System Imaging;" U.S. Pat. No. 5,543,133 for "Process of Preparing X-Ray Contrast Compositions Containing Nanoparticles;" U.S. Pat. No. 5,552,160 for "Surface Modified NSAID Nanoparticles;" U.S. Pat. No. 5,560,931 for "Formulations of Compounds as Nanoparticulate Dispersions in Digestible Oils or Fatty Acids;" U.S. Pat. No. 5,565,188 for "Polyalkylene Block Copolymers as Surface Modifiers for Nanoparticles;" U.S. Pat. No. 5,569,448 for "Sulfated Non-ionic Block Copolymer Surfactant as Stabilizer Coatings for Nanoparticle Compositions;" U.S. Pat. No. 5,571,536 for "Formulations of Compounds as Nanoparticulate Dispersions in Digestible Oils or Fatty Acids;" U.S. Pat. No. 5,573,749 for "Nanoparticulate Diagnostic Mixed Carboxylic Anydrides as X-Ray Contrast Agents for Blood Pool and Lymphatic System Imaging;" U.S. Pat. No. 5,573,750 for "Diagnostic Imaging X-Ray Contrast Agents;" U.S. Pat. No. 5,573,783 for "Redispersible Nanoparticulate Film Matrices With Protective Overcoats;" U.S. Pat. No. 5,580,579 for "Site-specific Adhesion Within the GI Tract Using Nanoparticles Stabilized by High Molecular Weight, Linear Poly(ethylene Oxide) Polymers;" U.S. Pat. No. 5,585,108 for "Formulations of Oral Gastrointestinal Therapeutic Agents in Combination with Pharmaceutically Acceptable Clays;" U.S. Pat. No. 5,587,143 for "Butylene Oxide-Ethylene Oxide Block Copolymers Surfactants as Stabilizer Coatings for Nanoparticulate Compositions;" U.S. Pat. No. 5,591,456 for "Milled Naproxen with Hydroxypropyl Cellulose as Dispersion Stabilizer;" U.S. Pat. No. 5,593,657 for "Novel Barium Salt Formulations Stabilized by Non-ionic and Anionic Stabilizers;" U.S. Pat. No. 5,622,938 for "Sugar Based Surfactant for Nanocrystals;" U.S. Pat. No. 5,628,981 for "Improved Formulations of Oral Gastrointestinal Diagnostic X-Ray Contrast Agents and Oral Gastrointestinal Therapeutic Agents;" U.S. Pat. No. 5,643,552 for "Nanoparticulate Diagnostic Mixed Carbonic Anhydrides as X-Ray Contrast Agents for Blood Pool and Lymphatic System Imaging;" U.S. Pat. No. 5,718,388 for "Continuous Method of Grinding Pharmaceutical Substances;" U.S. Pat. No. 5,718,919 for "Nanoparticles Containing the R(−) Enantiomer of Ibuprofen;" U.S. Pat. No. 5,747,001 for "Aerosols Containing Beclomethasone Nanoparticle Dispersions;" U.S. Pat. No. 5,834,025 for "Reduction of Intravenously Administered Nanoparticulate Formulation Induced Adverse Physiological Reactions;" U.S. Pat.

No. 6,045,829 "Nanocrystalline Formulations of Human Immunodeficiency Virus (HIV) Protease Inhibitors Using Cellulosic Surface Stabilizers;" U.S. Pat. No. 6,068,858 for "Methods of Making Nanocrystalline Formulations of Human Immunodeficiency Virus (HIV) Protease Inhibitors Using Cellulosic Surface Stabilizers;" U.S. Pat. No. 6,153,225 for "Injectable Formulations of Nanoparticulate Naproxen;" U.S. Pat. No. 6,165,506 for "New Solid Dose Form of Nanoparticulate Naproxen;" U.S. Pat. No. 6,221,400 for "Methods of Treating Mammals Using Nanocrystalline Formulations of Human Immunodeficiency Virus (HIV) Protease Inhibitors;" U.S. Pat. No. 6,264,922 for "Nebulized Aerosols Containing Nanoparticle Dispersions;" U.S. Pat. No. 6,267,989 for "Methods for Preventing Crystal Growth and Particle Aggregation in Nanoparticle Compositions;" U.S. Pat. No. 6,270,806 for "Use of PEG-Derivatized Lipids as Surface Stabilizers for Nanoparticulate Compositions;" U.S. Pat. No. 6,316,029 for "Rapidly Disintegrating Solid Oral Dosage Form," U.S. Pat. No. 6,375,986 for "Solid Dose Nanoparticulate Compositions Comprising a Synergistic Combination of a Polymeric Surface Stabilizer and Dioctyl Sodium Sulfosuccinate;" U.S. Pat. No. 6,428,814 for "Bioadhesive Nanoparticulate Compositions Having Cationic Surface Stabilizers;" U.S. Pat. No. 6,431,478 for "Small Scale Mill;" U.S. Pat. No. 6,432,381 for "Methods for Targeting Drug Delivery to the Upper and/or Lower Gastrointestinal Tract," U.S. Pat. No. 6,592,903 for "Nanoparticulate Dispersions Comprising a Synergistic Combination of a Polymeric Surface Stabilizer and Dioctyl Sodium Sulfosuccinate," U.S. Pat. No. 6,582,285 for "Apparatus for sanitary wet milling;" U.S. Pat. No. 6,656,504 for "Nanoparticulate Compositions Comprising Amorphous Cyclosporine;" U.S. Pat. No. 6,742,734 for "System and Method for Milling Materials;" U.S. Pat. No. 6,745,962 for "Small Scale Mill and Method Thereof;" U.S. Pat. No. 6,811,767 for "Liquid droplet aerosols of nanoparticulate drugs;" U.S. Pat. No. 6,908,626 for "Compositions having a combination of immediate release and controlled release characteristics;" U.S. Pat. No. 6,969,529 for "Nanoparticulate compositions comprising copolymers of vinyl pyrrolidone and vinyl acetate as surface stabilizers;" and U.S. Pat. No. 6,976,647 for "System and Method for Milling Materials," U.S. Pat. No. 6,991,191 for "Method of Using a Small Scale Mill;" U.S. Pat. No. 7,101,576 for "Nanoparticulate Megestrol Formulation," U.S. Pat. No. 7,198,795 for "In vitro methods for evaluating the in vivo effectiveness of dosage forms of microparticulate of nanoparticulate active agent compositions;" U.S. Pat. No. 7,244,451 for "Methods of making nanoparticulate drug compositions comprising copolymers of vinyl pyrrolidone and vinyl acetate as surface stabilizers"; U.S. Pat. No. 7,276,249 for "Nanoparticulate Fibrate Formulations"; U.S. Pat. No. 7,288,267 for "Bioadhesive nanoparticulate compositions having cationic surface stabilizers"; U.S. Pat. No. 7,320,802 for "Methods of treatment using nanoparticulate fenofibrate compositions"; and U.S. Pat. No. 7,390,505 for "Nanoparticulate topiramate formulations", all of which are specifically incorporated by reference.

Nanoparticulate active agent compositions are also described in U.S. Patent Publication No. 20080152720 for "Nanoparticulate tacrolimus formulations"; U.S. Patent Publication No. 20080152585 for "Low viscosity liquid dosage forms"; U.S. Patent Publication No. 20080138424 for "Nanoparticulate fibrate formulations"; U.S. Patent Publication No. 20080124393 for "Controlled release nanoparticulate compositions"; U.S. Patent Publication No. 20080124389 for "Nanoparticulate and Controlled Release Compositions Comprising Cyclosporine"; U.S. Patent Publication No. 20080113025 for "Compositions Comprising Nanoparticulate Naproxen and Controlled Release Hydrocodone"; U.S. Patent Publication No. 20080107741 for "Nanoparticulate Compositions of Angiogenesis Inhibitors"; U.S. Patent Publication No. 20080102121 for "Compositions Comprising Nanoparticulate Meloxicam and Controlled Release Hydrocodone"; U.S. Patent Publication No. 20080095851 for "Nanoparticulate fibrate formulations"; U.S. Patent Publication No. 20080050461 for "Nanoparticulate Compositions of Angiogenesis Inhibitors"; U.S. Patent Publication No. 20080025807 for "System and Method for Milling Materials"; U.S. Patent Publication No. 20080003295 for "Bioadhesive nanoparticulate compositions having cationic surface stabilizers"; U.S. Patent Publication No. 20070298115 for "Nanoparticulate fibrate formulations"; U.S. Patent Publication No. 20070298098 for "Controlled Release Compositions Comprising Levetiracetam"; U.S. Patent Publication No. 20070281011 for "Nanoparticulate posaconazole formulations"; U.S. Patent Publication No. 20070264348 for "Nanoparticulate fibrate formulations"; U.S. Patent Publication No. 20070224279 for "Stabilization of chemical compounds using nanoparticulate formulations"; U.S. Patent Publication No. 20070202180 for "Nanoparticulate carvedilol formulations"; U.S. Patent Publication No. 20070178051 for "Sterilized Nanoparticulate Glucocorticosteroid Formulations"; U.S. Patent Publication No. 20070160675 for "Nanoparticulate and controlled release compositions comprising a cephalosporin"; U.S. Patent Publication No. 20070148100 for "Nanoparticulate aripiprazole formulations"; U.S. Patent Publication No. 20070141159 for "Methods of Making Nanoparticulate Compositions Comprising Copolymers of Vinyl Pyrrolidone and Vinyl Acetate as Surface Stabilizers"; U.S. Patent Publication No. 20070134339 for "Zonisamide and NSAID Nanoparticulate Formulations"; U.S. Patent Publication No. 20070122486 for "Nanoparticulate insulin"; U.S. Patent Publication No. 20070110776 for "In vitro methods for evaluating the in vivo effectiveness of dosage forms of microparticulate or nanoparticulate active agent compositions;" U.S. Patent Publication No. 20070104792 for "Nanoparticulate tadalafil formulations;" U.S. Patent Publication No. 20070098805 for "Methods of making and using novel griseofulvin compositions;" U.S. Patent Publication No. 20070065374 for "Nanoparticulate leukotriene receptor antagonist/corticosteroid formulations;" U.S. Patent Publication No. 20070059371 for "Nanoparticulate ebastine formulations;" U.S. Patent Publication No. 20070048378 for "Nanoparticulate anticonvulsant and immunosuppressive compositions;" U.S. Patent Publication No. 20070042049 for "Nanoparticulate benidipine compositions;" U.S. Patent Publication No. 20070015719 for "Nanoparticulate clarithromycin formulations;" U.S. Patent Publication No. 20070003628 for "Nanoparticulate clopidogrel formulations;" U.S. Patent Publication No. 20070003615 for "Nanoparticulate clopidogrel and aspirin combination formulations;" U.S. Patent Publication No. 20060292214 for "Nanoparticulate acetaminophen formulations;" U.S. Patent Publication No. 20060275372 for "Nanoparticulate imatinib mesylate formulations;" U.S. Patent Publication No. 20060246142 for "Nanoparticulate quinazoline derivative formulations," U.S. Patent Publication No. 20060246141 for "Nanoparticulate lipase inhibitor formulations," U.S. Patent Publication No. 20060216353 for "Nanoparticulate corticosteroid and antihistamine formulations," U.S. Patent Publication No. 20060210639 for" Nanoparticulate bisphosphonate compositions," U.S. Patent Publication No.

20060210638 for "Injectable compositions of nanoparticulate immunosuppressive compounds," U.S. Patent Publication No. 20060204588 for "Formulations of a nanoparticulate finasteride, dutasteride or tamsulosin hydrochloride, and mixtures thereof," U.S. Patent Publication No. 20060198896 for "Aerosol and injectable formulations of nanoparticulate benzodiazepine," U.S. Patent Publication No. 20060193920 for "Nanoparticulate Compositions of Mitogen-Activated (MAP) Kinase Inhibitors," U.S. Patent Publication No. 20060188566 for "Nanoparticulate formulations of docetaxel and analogues thereof," U.S. Patent Publication No. 20060165806 for "Nanoparticulate candesartan formulations," "U.S. Patent Publication No. 20060159767 for "Nanoparticulate bicalutamide formulations," U.S. Patent Publication No. 20060159766 for "Nanoparticulate tacrolimus formulations," U.S. Patent Publication No. 20060159628 for "Nanoparticulate benzothiophene formulations," U.S. Patent Publication No. 20060154918 for "Injectable nanoparticulate olanzapine formulations," U.S. Patent Publication No. 20060121112 for "Topiramate pharmaceutical composition," U.S. Patent Publication No. 20020012675 A1, for "Controlled Release Nanoparticulate Compositions," U.S. Patent Publication No. 20040195413 A1, for "Compositions and method for milling materials," U.S. Patent Publication No. 20040173696 A1 for "Milling microgram quantities of nanoparticulate candidate compounds," U.S. Patent Application No. 20020012675 A1, published on Jan. 31, 2002, for "Controlled Release Nanoparticulate Compositions;" U.S. Patent Publication No. 20050276974 for "Nanoparticulate Fibrate Formulations;" U.S. Patent Publication No. 20050238725 for "Nanoparticulate compositions having a peptide as a surface stabilizer;" U.S. Patent Publication No. 20050233001 for "Nanoparticulate megestrol formulations;" U.S. Patent Publication No. 20050147664 for "Compositions comprising antibodies and methods of using the same for targeting nanoparticulate active agent delivery;" U.S. Patent Publication No. 20050063913 for "Novel metaxalone compositions;" U.S. Patent Publication No. 20050042177 for "Novel compositions of sildenafil free base;" U.S. Patent Publication No. 20050031691 for "Gel stabilized nanoparticulate active agent compositions;" U.S. Patent Publication No. 20050019412 for "Novel glipizide compositions;" U.S. Patent Publication No. 20050004049 for "Novel griseofulvin compositions;" U.S. Patent Publication No. 20040258758 for "Nanoparticulate topiramate formulations;" U.S. Patent Publication No. 20040258757 for "Liquid dosage compositions of stable nanoparticulate active agents;" U.S. Patent Publication No. 20040229038 for "Nanoparticulate meloxicam formulations;" U.S. Patent Publication No. 20040208833 for "Novel fluticasone formulations;" U.S. Patent Publication No. 20040195413 for "Compositions and method for milling materials;" U.S. Patent Publication No. 20040156895 for "Solid dosage forms comprising pullulan;" U.S. Patent Publication No. U.S. Patent Publication No. U.S. Patent Publication No. 20040156872 for "Novel nimesulide compositions;" U.S. Patent Publication No. 20040141925 for "Novel triamcinolone compositions;" U.S. Patent Publication No. 20040115134 for "Novel nifedipine compositions;" U.S. Patent Publication No. 20040105889 for "Low viscosity liquid dosage forms;" U.S. Patent Publication No. 20040105778 for "Gamma irradiation of solid nanoparticulate active agents;" U.S. Patent Publication No. 20040101566 for "Novel benzoyl peroxide compositions;" U.S. Patent Publication No. 20040057905 for "Nanoparticulate beclomethasone dipropionate compositions;" U.S. Patent Publication No. 20040033267 for "Nanoparticulate compositions of angiogenesis inhibitors;" U.S. Patent Publication No. 20040033202 for "Nanoparticulate sterol formulations and novel sterol combinations;" U.S. Patent Publication No. 20040018242 for "Nanoparticulate nystatin formulations;" U.S. Patent Publication No. 20040015134 for "Drug delivery systems and methods;" U.S. Patent Publication No. 20030232796 for "Nanoparticulate polycosanol formulations & novel polycosanol combinations;" U.S. Patent Publication No. 20030215502 for "Fast dissolving dosage forms having reduced friability;" U.S. Patent Publication No. 20030185869 for "Nanoparticulate compositions having lysozyme as a surface stabilizer;"U.S. Patent Publication No. 20030181411 for "Nanoparticulate compositions of mitogen-activated protein (MAP) kinase inhibitors;" U.S. Patent Publication No. 20030137067 for "Compositions having a combination of immediate release and controlled release characteristics;" U.S. Patent Publication No. 20030108616 for "Nanoparticulate compositions comprising copolymers of vinyl pyrrolidone and vinyl acetate as surface stabilizers;" U.S. Patent Publication No. 20030095928 for "Nanoparticulate insulin;" U.S. Patent Publication No. 20030087308 for "Method for high through put screening using a small scale mill or microfluidics;" U.S. Patent Publication No. 20030023203 for "Drug delivery systems & methods;" U.S. Patent Publication No. 20020179758 for "System and method for milling materials; and U.S. Patent Publication No. 20010053664 for "Apparatus for sanitary wet milling," describe nanoparticulate active agent compositions and are specifically incorporated by reference.

Amorphous small particle compositions are described, for example, in U.S. Pat. No. 4,783,484 for "Particulate Composition and Use Thereof as Antimicrobial Agent;" 4,826,689 for "Method for Making Uniformly Sized Particles from Water-Insoluble Organic Compounds;" 4,997,454 for "Method for Making Uniformly-Sized Particles From Insoluble Compounds;" 5,741,522 for "Ultrasmall, Non-aggregated Porous Particles of Uniform Size for Entrapping Gas Bubbles Within and Methods;" and 5,776,496, for "Ultrasmall Porous Particles for Enhancing Ultrasound Back Scatter." These disclosures are also specifically incorporated by reference.

None of these references describe the phenomenon of reducing "flake-like" aggregation in a nanoparticulate composition or a mechanism of reducing the same.

B. Background Regarding Injectable Formulations

The skilled person knows that for any particulate composition to be approved by the FDA for intravenous (I.V.) or intramuscular (I.M.) administration, the composition must meet the standards set forth in General Chapter 788 of the United States Pharmacopeia ("USP<788>"). Specifically, in the United States, any particulate matter injectable solution must comply with the particle size and number requirements of USP<788>. That is, under the approved "Light Obscuration" test set forth in USP<788>, known as "Method 1," there must be: (i) no more than 6,000 particles in a particulate composition that are greater than 10 µm in size and (ii) no more than 600 particles that are greater than 25 µm in size. Under "Method 2," the Microscopy test, a particulate composition must contain (i) no more than 3,000 particles in a particulate composition that are greater than 10 µm in size and (ii) no more than 300 particles that are greater than 25 µm in size. The theorized large particles represent the presence of aggregates of individual particles which clump together. It is theorized that nano particulate formulations has an inherent propensity to form flake like aggregates ("FLA"), presumably caused by colloidal surface phenomena. The "FLA's" are presumably formed at the air—liquid interface as the aggregate morphology is extremely two dimensional in its overall shape. Such aggregates have commonly been observed using optical microscopy and scanning electron microscopy techniques, but have not been detected using light scattering based particle sizing techniques.

There is a need in the art to develop injectable nanoparticulate active agent formulations that are essentially free of "flake-like" particulates, that meet the USP<788> criteria for particulate mater, and that have better stability at room temperature. Ideally, the formulations are ready-for-use, i.e., do not require reconstitution, and are suitable for conventional sterilization process. The present invention satisfies these needs.

SUMMARY OF THE INVENTION

The present invention relates to reduction of flake-like aggregation in injectable nanoparticulate active agent compositions. The composition comprises a nanoparticulate active agent, at least one surface stabilizer and a flake-like aggregation reducing agent. The surface stabilizer can be adsorbed on or associated with the surface of the active agent particles. The nanoparticulate active agent particles have an effective average particle size of less than about 2000 nm.

A preferred dosage form of the invention is an injectable nanoparticulate active agent colloidal dispersion. The composition optionally comprises one or more pharmaceutically acceptable carriers, as well as any desired excipients. Preferably, the nanoparticulate active agent colloidal dispersion is sterilized by passing through a filter having a pore size of 0.2 μm.

In one embodiment, the flake-like aggregation reducing agent is a sugar or polyol, such as sucrose, mannitol, or dextrose. In another embodiment, the flake-like aggregation reducing agent is a buffer, such as a potassium phosphate buffer, a sodium phosphate buffer, or a sodium acetate buffer. In one embodiment, the buffer results in the composition having a pH above 7.0. Compositions according to the invention can comprise more than one flake-like aggregation reducing agent, such as a combination of a sugar and a buffer.

In a related aspect, this invention further discloses a method of making the inventive nanoparticulate active agent compositions. Such a method comprises contacting the active agent with at least one surface stabilizer in the presence of a flake-like aggregation reducing agent for a time and under conditions sufficient to provide a nanoparticulate active agent composition having an effective average particle size of less than about 2000 nm. Alternatively, the surface stabilizer and/or flake-like aggregation reducing agent can be contacted with the active agent particles either before, during, or after particle size reduction of the active agent particles.

In another aspect, the invention relates to a method for reducing the flake-like aggregates in a nanoparticulate composition. The method comprises preparing a nanoparticulate dispersion of an active agent and adding a flake-like aggregation reducing agent to the dispersion. Alternatively, a nanoparticulate dispersion of an active agent is prepared in the presence of a flake-like aggregation reducing agent.

In yet another aspect, the invention relates to a method for reducing the flake-like aggregates in a nanoparticulate composition to meet the requirements of USP <788>. The method comprises preparing a nanoparticulate dispersion of an active agent and adding a flake-like aggregation reducing agent to the dispersion. Alternatively, a nanoparticulate dispersion of an active agent is prepared in the presence of a flake-like aggregation reducing agent.

In a further aspect, the invention relates to a method of treatment using a nanoparticulate active agent composition according to the invention. The method comprises administering a nanoparticulate active agent composition according to the invention, comprising at least one nanoparticulate active agent, at least one surface stabilizer, and at least one flake-like aggregation reducing agent to a subject in need. The condition to be treated can be any condition susceptible to treatment by the active agent present in the nanoparticulate composition.

Both the foregoing summary of the invention and the following brief description of the drawings and detailed description of the invention are exemplary and explanatory and are intended to provide further details of the invention as claimed. Other objects, advantages, and novel features will be readily apparent to those skilled in the art from the following detailed description of the invention.

BRIEF DESCRIPTION OF THE DRAWINGS

The patent or application file contains at least one or more drawings executed in color. Copies of this patent or patent application publication with color drawing(s) will be provided by the Office upon request and payment of the necessary fee.

DETAILED DESCRIPTION OF THE INVENTION

The present invention relates to reduction of flake-like aggregation in nanoparticulate compositions. The composition comprises a nanoparticulate active agent having an effective average particle size of less than about 2000 nm, at least one surface stabilizer adsorbed on or associated with the surface of the active agent particles and a flake-like aggregation reducing agent.

Figure 1:
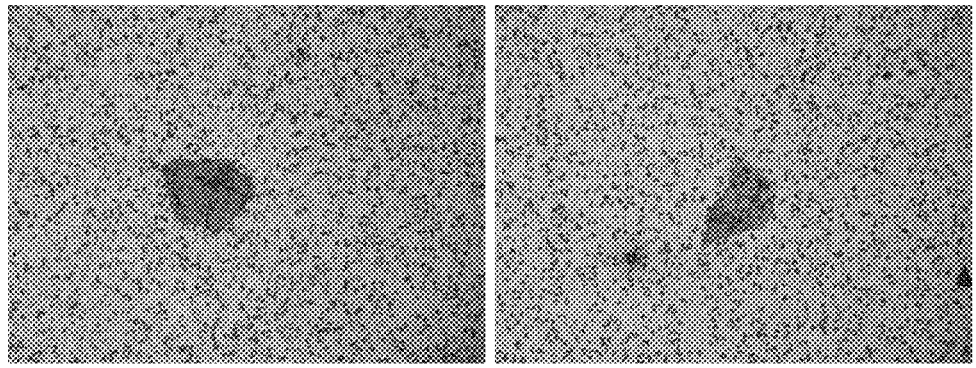
FIG. 1 shows the images of flake-like particulates in NCD™ formulations.
Figure 2:
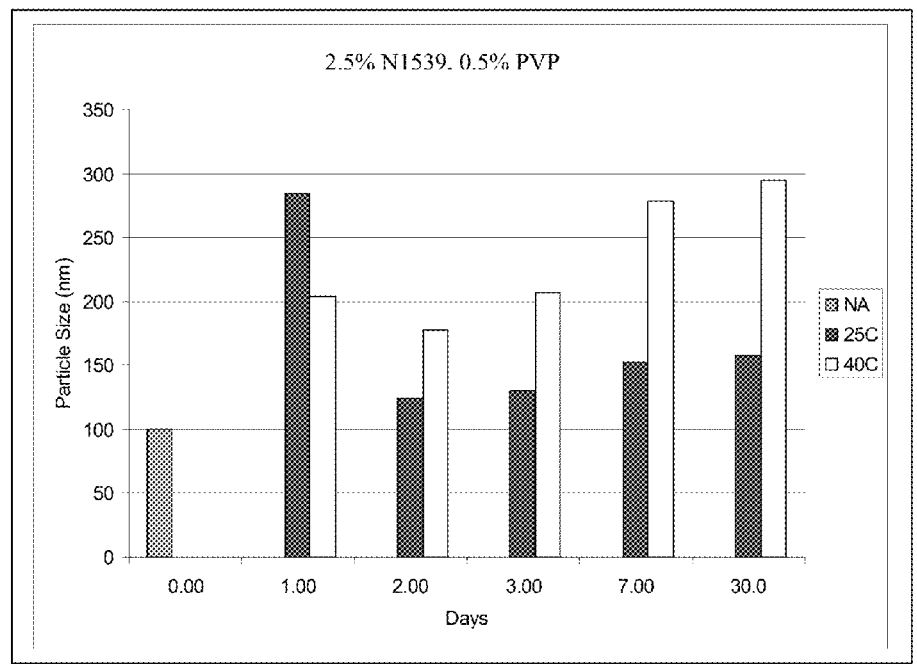
FIG. 2 shows the particle size of a formulation containing 2.5% meloxicam and 0.5% PVP K17 at 25° C. and 40° C. storage for up to a month.
Figure 3:
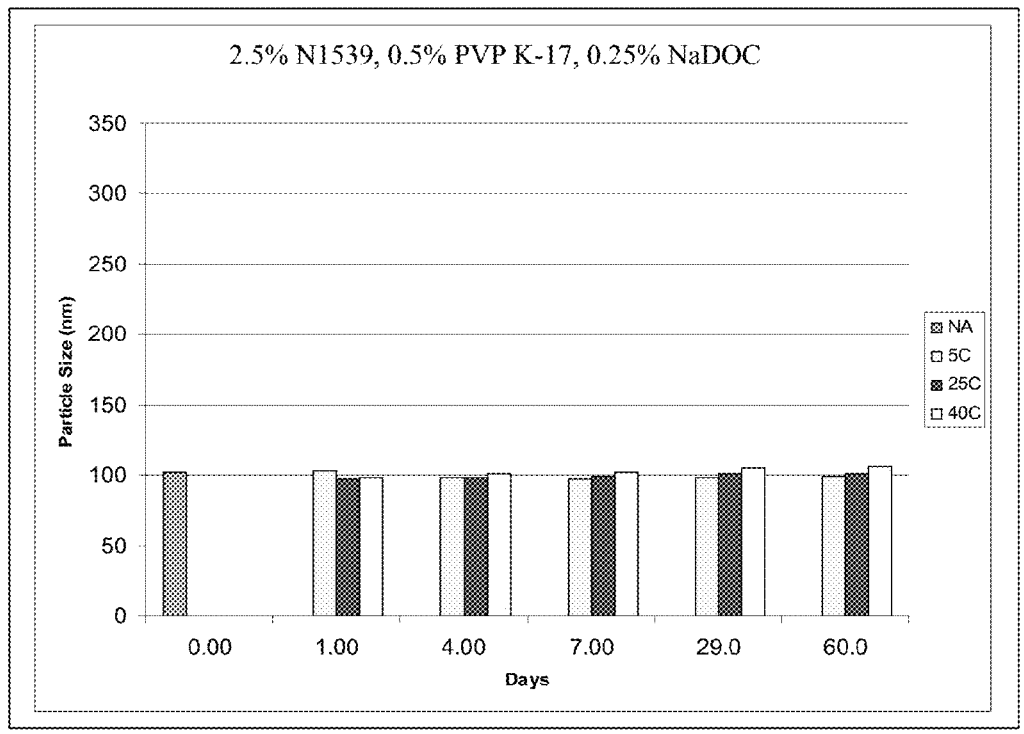
FIG. 3 shows the particle size of a formulation containing 2.5% meloxicam, 0.5% PVP K17 and 0.25% NaDOC at 5° C., 25° C. and 40° C. storage for up to two months.
Figure 4:
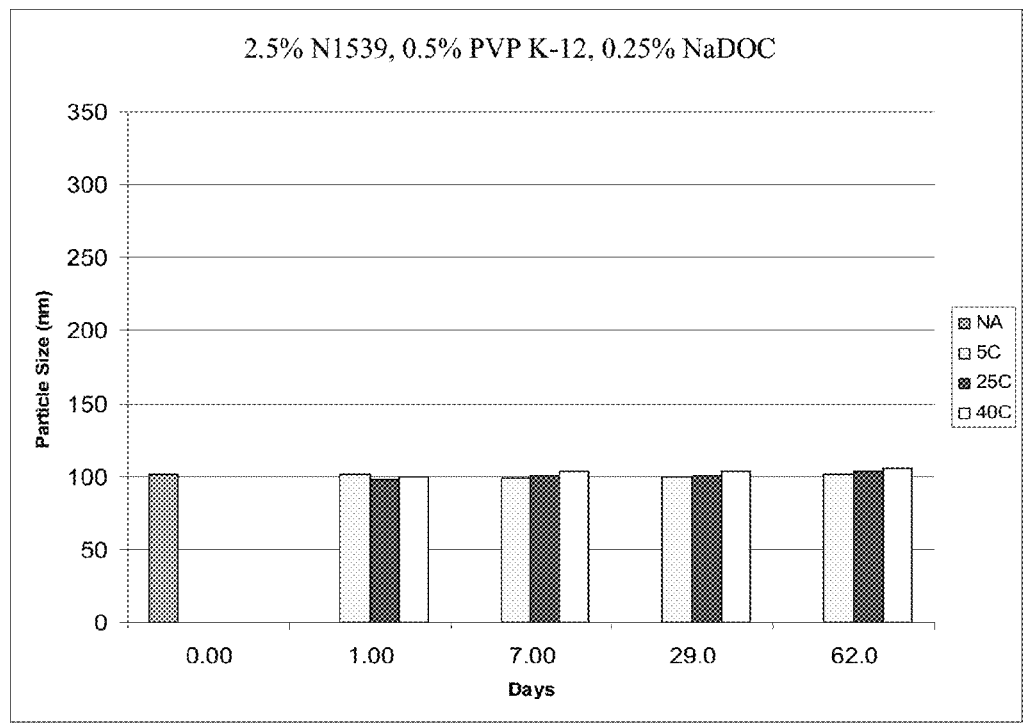
FIG. 4 shows the particle size of a formulation containing 2.5% meloxicam, 0.5% PVP K12 and 0.25% NaDOC at 5° C., 25° C. and 40° C. storage for up to two months.
Figure 5:
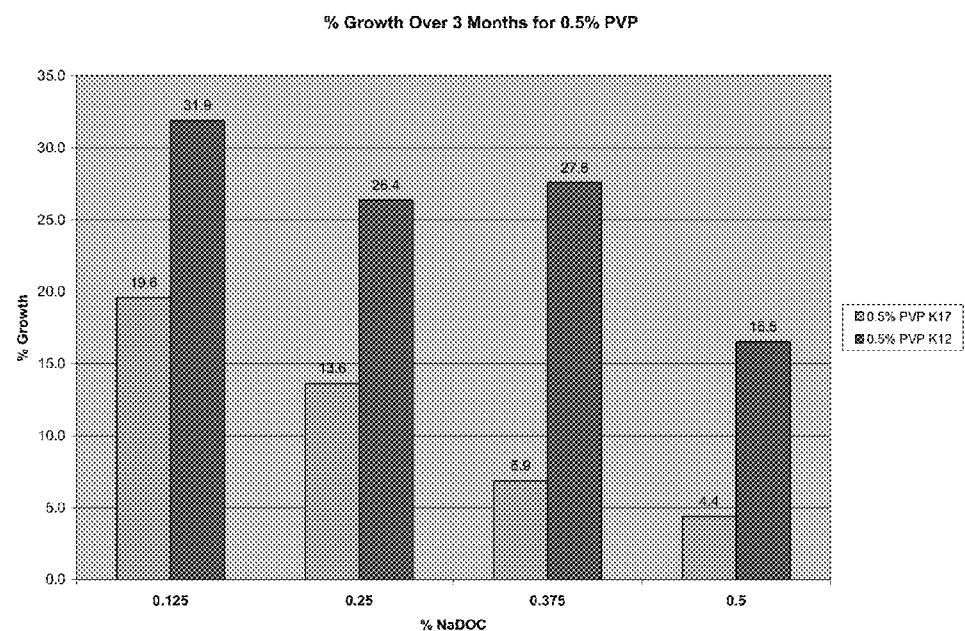
FIG. 5 shows the particle size growth in the presence of 0.5% PVP at variable concentration of NaDOC for over 3 months.
Figure 6:
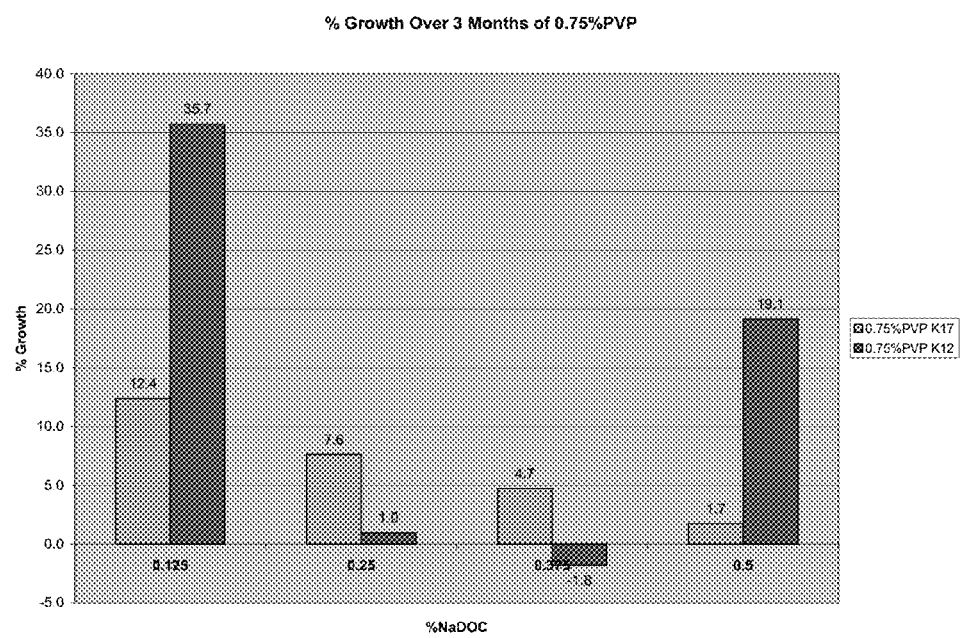
FIG. 6 shows the particle size growth in the presence of 0.75% PVP at variable concentration of NaDOC for over 3 months.

As taught in the '684 patent, not every combination of surface stabilizer and active agent will result in a stable nanoparticulate composition. The particulate matter test performed on some nanocrystalline formulations using the filtration/microscopy method as per USP<788> found high level of "flake-like particulates" as shown in FIG. 1. These formulations fail to meet the USP<788> criteria.

One problem present in prior art formulations of injectable dosage forms is the need for solubilizing solvents, such as cremofor, or in aqueous solvents that may contain co-solvents and/or involve harsh pH conditions, all which may present significant toxicity upon administration. Such formulations may still require large injection volumes, which further adds to the toxicity of the drug product. Injectable dosage forms of poorly soluble drugs that can be administered in aqueous based media in high concentration without requiring harsh pH conditions or co-solvents are highly desirable.

An exemplary active agent that can be utilized in the formulations of the invention is meloxicam. Meloxicam (CAS No. 71125-38-7), chemically known as 4-hydroxy-2-methyl-N-(5-methyl-2-thiazolyl)-2H-1,2-benzothiazine-3-carboxamide-1, 1-dioxide, has an empiric formula of $C_{14}H_{13}N_3O_4S_2$ and a molecular weight of 351.403. Meloxicam is a pale yellow crystalline powder with no odor. Practically insoluble in water. The melting point is 254° C.

Meloxicam belongs to the family of nonsteroidal anti-inflammatory drugs (NSAIDs) and is used to relieve the symptoms of arthritis, primary dysmenorrheal, fever, and as an analgesic, especially where there is an inflammatory component.

Development of a nanoparticulate colloidal dispersion of meloxicam suitable for injection encountered difficulty because it contained "flake-like" particulates ranging from 10-600 μm, which failed to meet the USP<788> standard.

Thus, the discovery of the present invention is surprising in that a flake-like aggregation reducing agent could be successfully used to reduce aggregation of the particles of the nanoparticulate active agent. The obtained nanoparticulate active agent composition meets the criteria of USP<788> and is suitable for injection.

I. Definitions

The present invention is described herein using several definitions, as set forth below and throughout the application.

As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

"Nanoparticulate active agents" as defined herein have an effective average particle size of less than about 2 microns.

"Pharmaceutically acceptable" as used herein refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein with reference to stable drug particles, "stable" includes, but is not limited to, one or more of the following parameters: (1) that the active agent particles do not appreciably flocculate or agglomerate due to interparticle attractive forces, or otherwise significantly increase in particle size over time; (2) that the physical structure of the active agent particles is not altered over time, such as by conversion from an amorphous phase to crystalline phase or convert from one polymorph and/or hydrate to another; (3) that the active agent particles are chemically stable; and/or (4) where the active agent has not been subject to a heating step at or above the melting point of the active agent in the preparation of the nanoparticles of the invention.

"Therapeutically effective amount" as used herein with respect to an active agent dosage, shall mean that dosage that provides the specific pharmacological response for which the active agent is administered in a significant number of subjects in need of such treatment. It is emphasized that "therapeutically effective amount," administered to a particular subject in a particular instance will not always be effective in treating the diseases described herein, even though such dosage is deemed a 'therapeutically effective amount' by those skilled in the art. It is to be further understood that active agent dosages are, in particular instances, measured as oral dosages, or with reference to active agent levels as measured in blood.

II. Compositions

The compositions of the invention comprise a nanoparticulate active agent, at least one surface stabilizer adsorbed to or associated with the surface of the active agent, and at least one flake-like aggregation reducing agent. In addition, the compositions can comprise one or more secondary flake-like aggregation reducing agent. Surface stabilizers useful herein physically adhere to or associate with the surface of the nanoparticulate active agent but do not chemically react with the active agent or itself. Individual molecules of the surface stabilizer are essentially free of intermolecular cross-linkages.

The present invention also includes nanoparticulate active agent compositions formulated into compositions together with one or more non-toxic physiologically acceptable carriers, adjuvants, or vehicles, collectively referred to as carriers.

A. Active Agents

The nanoparticles of the invention comprise at least one active, therapeutic, or diagnostic agent, collectively referred to as a "drug." A therapeutic agent can be a pharmaceutical agent, including biologics such as proteins, peptides, and nucleotides, or a diagnostic agent, such as a contrast agent, including x-ray contrast agents.

The active agent exists as a crystalline phase, an amorphous phase, a semi-amorphous phase, a semi-crystalline phase, or mixtures thereof. The crystalline phase differs from a non-crystalline or amorphous phase which results from precipitation techniques, such as those described in EP Patent No. 275,796.

The invention can be practiced with a wide variety of active agents. The active agent is preferably present in an essentially pure form, is poorly soluble, and is dispersible in at least one liquid dispersion media. By "poorly soluble" it is meant that the active agent has a solubility in a liquid dispersion media of less than about 30 mg/mL, less than about 20 mg/mL, less than about 10 mg/mL, or less than about 1 mg/mL. Useful liquid dispersion medias include, but are not limited to, water, aqueous salt solutions, safflower oil, and solvents such as ethanol, t-butanol, hexane, and glycol. A preferred liquid dispersion media is water.

Two or more active agents can be used in combination.

1. Active Agents Generally

The active agent can be selected from a variety of known classes of drugs, including, for example, nutraceuticals, COX-2 inhibitors, retinoids, anticancer agents, NSAIDS, proteins, peptides, nucleotides, anti-obesity drugs, nutraceuticals, dietary supplements, carotenoids, corticosteroids, elastase inhibitors, anti-fungals, oncology therapies, anti-emetics, analgesics, cardiovascular agents, anti-inflammatory agents, anthelmintics, anti-arrhythmic agents, antibiotics (including penicillins), anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytics, sedatives (hypnotics and neuroleptics), astringents, beta-adrenoceptor blocking agents, blood products and substitutes, cardiac inotropic agents, contrast media, corticosteroids, cough suppressants (expectorants and mucolytics), diagnostic agents, diagnostic imaging agents, diuretics, dopaminergics (antiparkinsonian agents), haemostatics, immunological agents, lipid regulating agents, muscle relaxants, parasympathomimetics, parathyroid calcitonin and biphosphonates, prostaglandins, radio-pharmaceuticals, sex hormones (including steroids), anti-allergic agents, stimulants and anoretics, sympathomimetics, thyroid agents, vasodilators, and xanthines.

Examples of representative active agents useful in this invention include, but are not limited to, acyclovir, alprazolam, altretamine, amiloride, amiodarone, benztropine mesylate, bupropion, cabergoline, candesartan, cerivastatin, chlorpromazine, ciprofloxacin, cisapride, clarithromycin, clonidine, clopidogrel, cyclobenzaprine, cyproheptadine, delavirdine, desmopressin, diltiazem, dipyridamole, dolasetron, enalapril maleate, enalaprilat, famotidine, felodipine, furazolidone, glipizide, irbesartan, ketoconazole, lansoprazole, loratadine, loxapine, mebendazole, mercaptopurine, milrinone lactate, minocycline, mitoxantrone, nelfinavir mesylate, nimodipine, norfloxacin, olanzapine, omeprazole, penciclovir, pimozide, tacrolimus, quazepam, raloxifene, rifabutin, rifampin, risperidone, rizatriptan, saquinavir, sertraline, sildenafil, acetyl-sulfisoxazole, temazepam, thiabendazole, thioguanine, trandolapril, triamterene, trimetrexate, troglitazone, trovafloxacin, verapamil, vinblastine sulfate, mycophenolate, atovaquone, proguanil, ceftazidime, cefuroxime, etoposide, terbinafine, thalidomide, fluconazole, amsacrine, dacarbazine, teniposide, and acetylsalicylate. In one embodiment, the active agent is meloxicam.

Exemplary nutraceuticals and dietary supplements are disclosed, for example, in Roberts et al., *Nutraceuticals: The Complete Encyclopedia of Supplements, Herbs, Vitamins, and Healing Foods* (American Nutraceutical Association, 2001), which is specifically incorporated by reference. A nutraceutical or dietary supplement, also known as a phytochemical or functional food, is generally any one of a class of dietary supplements, vitamins, minerals, herbs, or healing foods that have medical or pharmaceutical effects on the body. Exemplary nutraceuticals or dietary supplements include, but are not limited to, lutein, folic acid, fatty acids (e.g., DHA and ARA), fruit and vegetable extracts, vitamin and mineral supplements, phosphatidylserine, lipoic acid, melatonin, glucosamine/chondroitin, Aloe Vera, Guggul, glutamine, amino acids (e.g., iso-leucine, leucine, lysine, methionine, phenylanine, threonine, tryptophan, and valine), green tea, lycopene, whole foods, food additives, herbs, phytonutrients, antioxidants, flavonoid constituents of fruits, evening primrose oil, flax seeds, fish and marine animal oils, and probiotics. Nutraceuticals and dietary supplements also include bio-engineered foods genetically engineered to have a desired property, also known as "pharmafoods."

2. Anticancer Active Agents

Useful anticancer agents are preferably selected from alkylating agents, antimetabolites, natural products, hormones and antagonists, and miscellaneous agents, such as radiosensitizers.

Examples of alkylating agents include: (1) alkylating agents having the bis-(2-chloroethyl)-amine group such as, for example, chlormethine, chlorambucile, melphalan, uramustine, mannomustine, extramustinephoshate, mechlorethaminoxide, cyclophosphamide, ifosfamide, and trifosfamide; (2) alkylating agents having a substituted aziridine group such as, for example, tretamine, thiotepa, triaziquone, and mitomycine; (3) alkylating agents of the alkyl sulfonate type, such as, for example, busulfan, piposulfan, and piposulfam; (4) alkylating N-alkyl-N-nitrosourea derivatives, such as, for example, carmustine, lomustine, semustine, or streptozotocine; and (5) alkylating agents of the mitobronitole, dacarbazine and procarbazine type.

Examples of antimetabolites include: (1) folic acid analogs, such as, for example, methotrexate; (2) pyrimidine analogs such as, for example, fluorouracil, floxuridine, tegafur, cytarabine, idoxuridine, and flucytosine; and (3) purine derivatives such as, for example, mercaptopurine, thioguanine, azathioprine, tiamiprine, vidarabine, pentostatin, and puromycine.

Examples of natural products include: (1) vinca alkaloids, such as, for example, vinblastine and vincristine; (2) epipodophylotoxins, such as, for example, etoposide and teniposide; (3) antibiotics, such as, for example, adriamycine, daunomycine, doctinomycin, daunorubicin, doxorubicin, mithramycin, bleomycin, and mitomycin; (4) enzymes, such as, for example, L-asparaginase; (5) biological response modifiers, such as, for example, alpha-interferon; (6) camptothecin; (7) taxol; and (8) retinoids, such as retinoic acid.

Examples of hormones and antagonists include: (1) adrenocorticosteroids, such as, for example, prednisone; (2) progestins, such as, for example, hydroxyprogesterone caproate, medroxyprogesterone acetate, and megestrol acetate; (3) estrogens, such as, for example, diethylstilbestrol and ethinyl estradiol; (4) antiestrogens, such as, for example, tamoxifen; (5) androgens, such as, for example, testosterone propionate and fluoxymesterone; (6) antiandrogens, such as, for example, flutamide; and (7) gonadotropin-releasing hormone analogs, such as, for example, leuprolide.

Examples of miscellaneous agents include: (1) radiosensitizers, such as, for example, 1,2,4-benzotriazin-3-amine 1,4-dioxide (SR 4889) and 1,2,4-benzotriazine-7-amine 1,4-dioxide (WIN 59075); (2) platinum coordination complexes such as cisplatin and carboplatin; (3) anthracenediones, such as, for example, mitoxantrone; (4) substituted ureas, such as, for example, hydroxyurea; and (5) adrenocortical suppressants, such as, for example, mitotane and aminoglutethimide.

In addition, the anticancer agent can be an immunosuppressive drug, such as, for example, cyclosporine, azathioprine, sulfasalazine, methoxsalen, and thalidomide.

The anticancer agent can also be a COX-2 inhibitor.

3. Analgesic Active Agents

An analgesic can be, for example, an NSAID or a COX-2 inhibitor.

Exemplary NSAIDS that can be formulated in compositions of the invention include, but are not limited to, suitable nonacidic and acidic compounds. Suitable nonacidic compounds include, for example, nabumetone, tiaramide, proquazone, bufexamac, flumizole, epirazole, tinoridine, timegadine, and dapsone. Suitable acidic compounds include, for example, carboxylic acids and enolic acids. Suitable carboxylic acid NSAIDs include, for example: (1) salicylic acids and esters thereof, such as aspirin, diflunisal, benorylate, and fosfosal; (2) acetic acids, such as phenylacetic acids, including diclofenac, alclofenac, and fenclofenac; (3) carbo- and heterocyclic acetic acids such as etodolac, indomethacin, sulindac, tolmetin, fentiazac, and tilomisole; (4) propionic acids, such as carprofen, fenbufen, flurbiprofen, ketoprofen, oxaprozin, suprofen, tiaprofenic acid, ibuprofen, naproxen, fenoprofen, indoprofen, and pirprofen; and (5) fenamic acids, such as flufenamic, mefenamic, meclofenamic, and niflumic. Suitable enolic acid NSAIDs include, for example: (1) pyrazolones such as oxyphenbutazone, phenylbutazone, apazone, and feprazone; and (2) oxicams such as piroxicam, sudoxicam, isoxicam, and tenoxicam.

Exemplary COX-2 inhibitors that can be formulated in combination with the nanoparticulate nimesulide composition of the invention include, but are not limited to, celecoxib (SC-58635, CELEBREX®, Pharmacia/Searle & Co.), rofecoxib (MK-966, L-748731, VIOXX®, Merck & Co.), meloxicam (MOBIC®, co-marketed by Abbott Laboratories, Chicago, Ill., and Boehringer Ingelheim Pharmaceuticals), valdecoxib (BEXTRA®, G.D. Searle & Co.), parecoxib (G.D. Searle & Co.), etoricoxib (MK-663; Merck), SC-236 (chemical name of 4-[5-(4-chlorophenyl)-3-(trifluoromethyl)-1H-pyrazol-1-yl)] benzenesulfonamide; G.D. Searle & Co., Skokie, Ill.); NS-398 (N-(2-cyclohexyloxy-4-nitrophenyl)methane sulfonamide; Taisho Pharmaceutical Co., Ltd., Japan); SC-58125 (methyl sulfone spiro(2.4)hept-5-ene I; Pharmacia/Searle & Co.); SC-57666 (Pharmacia/Searle & Co.); SC-558 (Pharmacia/Searle & Co.); SC-560 (Pharmacia/Searle & Co.); etodolac (Lodine®, Wyeth-Ayerst Laboratories, Inc.); DFU (5,5-dimethyl-3-(3-fluorophenyl)-4-(4-methylsulfonyl)phenyl 2(5H)-furanone); monteleukast (MK-476), L-745337 ((5-methanesulphonamide-6-(2,4-difluorothio-phenyl)-1-indanone), L-761066, L-761000, L-748780 (all Merck & Co.); DUP-697 (5-Bromo-2-(4-fluorophenyl)-3-(4-(methylsulfonyl)phenyl; DuPont Merck Pharmaceutical Co.); PGV 20229 (1-(7-tert.-butyl-2,3-dihydro-3,3-dimethylbenzo(b)furan-5-yl)-4-cyclopropylbutan-1-one; Procter & Gamble Pharmaceuticals); iguratimod (T-614; 3-formylamino-7-methylsulfonylamino-6-phenoxy-4H-1-benzopyran-4-one; Toyama Corp., Japan); BF 389 (Biofor, USA); CL 1004 (PD 136095), PD 136005, PD 142893, PD 138387, and PD 145065 (all Parke-Davis/Warner-Lambert Co.); flurbiprofen (ANSAID®; Pharmacia & Upjohn); nabumetone (FELAFEN®; SmithKline Beecham, plc); flosulide (CGP 28238; Novartis/Ciba Geigy); piroxicam (FELDANE®; Pfizer); diclofenac (VOLTAREN® and CATAFLAM®, Novartis); lumiracoxib (COX-189; Novartis); D 1367 (Celltech Chiroscience, plc); R 807 (3 benzoyldifluoromethane sulfonanilide, diflumidone); JTE-522 (Japan Tobacco, Japan); FK-3311 (4'-Acetyl-2'-(2,4-difluorophenoxy)methanesulfonanilide), FK 867, FR 140423, and FR 115068 (all Fujisawa, Japan); GR 253035 (Glaxo Wellcome); RWJ 63556 (Johnson & Johnson); RWJ 20485 (Johnson & Johnson); ZK 38997 (Schering); S 2474 ((E)-(5)-(3,5-di-tert-butyl-4-hydroxybenzylidene)-2-ethyl-1,2-isothiazolidine-1,1-dioxide indomethacin; Shionogi & Co., Ltd., Japan); zomepirac analogs, such as RS 57067 and RS 104897 (Hoffmann La Roche); RS 104894 (Hoffmann La Roche); SC 41930 (Monsanto); pranlukast (SB 205312, Ono-1078, ONON®, ULTAIR®; SmithKline Beecham); SB 209670 (SmithKline Beecham); and APHS (heptinylsulfide).

B. Surface Stabilizers

The compositions of the invention include one or more surface stabilizers. The surface stabilizers of the invention are preferably adsorbed on, or associated with, the surface of the active agent particles. The surface stabilizers especially useful herein preferably do not chemically react with the active agent particles or itself. Preferably, individual molecules of the auxiliary surface stabilizer are essentially free of intermolecular cross-linkages.

Two or more surface stabilizers can be employed in the compositions and methods of the invention.

Suitable surface stabilizers can preferably be selected from known organic and inorganic pharmaceutical excipients. Such excipients include various polymers, low molecular weight oligomers, natural products, and surfactants. Preferred surface stabilizers include nonionic, anionic, cationic and zwitterionic compounds or surfactants.

Examples of useful nonionic stabilizers, including but not limited to, dextran, gum acacia, tragacanth, glycerol monostearate, cetostearyl alcohol, cetomacrogol emulsifying wax, sorbitan esters, polyoxyethylene alkyl ethers (e.g., macrogol ethers such as cetomacrogol 1000), polyoxyentylene alkyl esters (e.g. Myrj®), polyoxyethylene castor oil derivatives, polyoxyethylene sorbitan fatty acid esters (e.g., the commercially available Tweens® such as e.g., Tween 20® and Tween 80® (ICI Speciality Chemicals)); polyethylene glycols (e.g., Carbowaxs 3550® and 934® (Union Carbide)), polyoxyethylene stearates, methylcellulose, hydroxyethylcellulose, hydroxypropyl celluloses (e.g., HPC, HPC-SL, and HPC-L), hydroxypropyl methylcellulose (HPMC), hydroxypropylmethyl-cellulose phthalate, noncrystalline cellulose, triethanolamine, polyvinyl alcohol (PVA), polyvinylpyrrolidone (PVP), 4-(1,1,3,3-tetramethylbutyl)-phenol polymer with ethylene oxide and formaldehyde (also known as tyloxapol, superione, and triton), poloxamers (e.g., Pluronics F68® and F108®, which are block copolymers of ethylene oxide and propylene oxide); poloxamines (e.g., Tetronic 908®, also known as Poloxamine 908®, which is a tetrafunctional block copolymer derived from sequential addition of propylene oxide and ethylene oxide to ethylenediamine (BASF Wyandotte Corporation, Parsippany, N.J.)); Tetronic 1508® (T-1508) (BASF Wyandotte Corporation), alkyl phenol ethylene oxide (Triton X-100, Triton X-405, etc., Dow Chemical), Crodestas F-110®, which is a mixture of sucrose stearate and sucrose distearate (Croda Inc.); p-isononylphenoxypoly-(glycidol), also known as Olin-10G® or Surfactant 10-G® (Olin Chemicals, Stamford, Conn.); Crodestas SL-40® (Croda, Inc.); and SA9OHCO, which is $C_{18}H_{37}CH_2C(O)N(CH_3)—CH_2(CHOH)_4(CH_2OH)_2$ (Eastman Kodak Co.); decanoyl-N-methylglucamide; n-decyl β-D-glucopyranoside; n-decyl β-D-maltopyranoside; n-dodecyl β-D-glucopyranoside; n-dodecyl β-D-maltoside; heptanoyl-N-methylglucamide; n-heptyl-β-D-glucopyranoside; n-heptyl β-D-thioglucoside; n-hexyl β-D-glucopyranoside; nonanoyl-N-methylglucamide; n-noyl β-D-glucopyranoside; octanoyl-N-methylglucamide; n-octyl-β-D-glucopyranoside; octyl β-D-thioglucopyranoside; PEG-derivatized phospholipid, PEG-derivatized cholesterol, PEG-derivatized cholesterol derivative, PEG-derivatized vitamin A, PEG-derivatized vitamin E, PEG-derivatized castor oil (Cremafor), random copolymers of vinyl pyrrolidone and vinyl acetate (an example would be Plasdone S-630, ISP).

Preferred nonionic stabilizers include, but are not limited to, Hydroxypropyl methylcellulose (HPMC), hydroxypropyl cellulose grade HPC-SL, Polyvinylpyrrolidones, Kollidone K12 (BASF) or Plasdone® C-12 (ISP Technologies, Inc.) Kollidone K17 (BASF)-Plasdone® C-17 (ISP Technologies, Inc). Kollidone K29/32 (BASF)-Plasdone® C-29/32 (ISP Technologies, Inc. (USA), block copolymers based on ethylene oxide and propylene oxide—Poloxamers sold under the tradename Pluronics® by BASF (sold as Lutrols® in EU), specifically Pluronic® F 68 a.k.a. poloxamer 188, Pluronic® F 108 a.k.a. poloxamer 338, Pluronic® F 127 a.k.a poloxamer. 407, copolymer of vinylpyrrolidone and vinyl acetate—Copovidone sold under the tradename Plasdone® S-630 (ISP Technologies, Inc), distearyl palmitate glyceryl, polyoxyethylene sorbitan fatty acid esters such as polyoxyethylene 20 sorbitan monolaurate, polysorbate 20 a.k.a. Tween® 20 by ICI Americas, polyoxyethylene 20 sorbitan monopalmitate, polysorbate 40" a.k.a. Tween® 40 by ICI Americas, polyoxyethylene 20 sorbitan monooleate, polysortbate 80 a.k.a. Tween® 80 by ICI Americas, macrogol 15 hydroxystearate—Solutol® 15 BASF, Tyloxapol and Cremaphor.

Examples of useful anionic stabilizers, including but not limited to, fatty acids as well as their salt forms such as oleic acid, stearic acid, palmitic acid, lauric acid, myristic acid, calcium stearate. Other common anionic stabilizers include sodium dodecylsulfate, Duponol P®, which is a sodium lauryl sulfate (DuPont), carboxymethylcellulose calcium, carboxymethylcellulose sodium, dialkylesters of sodium sulfosuccinic acid (e.g., Aerosol OT®, which is a dioctyl ester of sodium sulfosuccinic acid (DOSS) (American Cyanamid)), Triton X-200®, which is an alkyl aryl polyether sulfonate (Union Carbide). Salt forms of bile acids are also useful as anionic stabilizers, such as sodium deoxycholate, sodium cholate, sodium chenodeoxycholate, sodium dehydrocholate, disuccinylursodeoxycholic acid bisodic salt, sodium hyodeoxycholate, sodium ursodeoxycholate.

Preferred anionic stabilizers include, but are not limited to, dioctyl sodium succinate (DOSS) sodium lauryl sulfate (SLS) a.k.a. sodium dodecyl sulfate (SDS) and sodium deoxycholate.

Examples of useful cationic surface stabilizers include but are not limited to polymers, biopolymers, poly-n-methyl-pyridinium, anthryul pyridinium chloride, cationic phospholipids, chitosan, polylysine, polyvinylimidazole, polybrene, polymethylmethacrylate trimethylammoniumbromide bromide (PMMTMABr), hexyldesyltrimethylammonium bromide (HDMAB), and polyvinylpyrrolidone-2-dimethylaminoethyl methacrylate dimethyl sulfate.

Other useful cationic stabilizers include, but are not limited to, cationic lipids, sulfonium, phosphonium, and quarternary ammonium compounds, such as stearyltrimethylammonium chloride, benzyl-di(2-chloroethyl)ethylammonium bromide, coconut trimethyl ammonium chloride or bromide, coconut methyl dihydroxyethyl ammonium chloride or bromide, dodecyl trimethyl ammonium bromide, decyl triethyl ammonium chloride, decyl dimethyl hydroxyethyl ammonium chloride or bromide, $C_{12-15}$ dimethyl hydroxyethyl ammonium chloride or bromide, coconut dimethyl hydroxyethyl ammonium chloride or bromide, myristyl trimethyl ammonium methyl sulphate, lauryl dimethyl benzyl ammonium chloride or bromide, lauryl dimethyl (ethenoxy)$_4$ ammonium chloride or bromide, N-alkyl ($C_{12-18}$)dimethylbenzyl ammonium chloride, N-alkyl ($C_{14-18}$) dimethyl-benzyl ammonium chloride, N-tetradecylidmethylbenzyl ammonium chloride monohydrate, dimethyl didecyl ammonium chloride, N-alkyl and ($C_{12-14}$) dimethyl 1-napthylmethyl ammonium chloride, trimethylammonium halide, alkyl-trimethylammonium salts and dialkyl-dimethylammonium salts, lauryl trimethyl ammonium chloride, ethoxylated alkyamidoalkyldialkylammonium salt and/or an ethoxylated trialkyl ammonium salt, dialkylbenzene dialkylammonium chloride, N-didecyldimethyl ammonium chloride, N-tetradecyldimethylbenzyl ammonium, chloride monohydrate, N-alkyl($C_{12-14}$) dimethyl 1-naphthylmethyl ammonium chloride and dodecyldimethylbenzyl ammonium chloride, dialkyl benzenealkyl ammonium chloride, lauryl trimethyl ammonium chloride, alkylbenzyl methyl ammonium chloride, alkyl benzyl dimethyl ammonium bromide, $C_{12}$, $C_{15}$, $C_{17}$ trimethyl ammonium bromides, dodecylbenzyl triethyl ammonium chloride, poly-diallyldimethylammonium chloride (DADMAC), dimethyl ammonium chlorides, alkyldimethylammonium halogenides, tricetyl methyl ammonium chloride, decyltrimethylammonium bromide, dodecyltriethylammonium bromide, tetradecyltrimethylammonium bromide, methyl trioctylammonium chloride (ALIQUAT 336™), POLYQUAT 10™, tetrabutylammonium bromide, benzyl trimethylammonium bromide, choline esters (such as choline esters of fatty acids), benzalkonium chloride, stearalkonium chloride compounds (such as stearyltrimonium chloride and Distearyldimonium chloride), cetyl pyridinium bromide or chloride, halide salts of quatemized polyoxyethylalkylamines, MIRAPOL™ and ALKAQUAT™ (Alkaril Chemical Company), alkyl pyridinium salts; amines, such as alkylamines, dialkylamines, alkanolamines, polyethylenepolyamines, N,N-dialkylaminoalkyl acrylates, and vinyl pyridine, amine salts, such as lauryl amine acetate, stearyl amine acetate, alkylpyridinium salt, and alkylimidazolium salt, and amine oxides; imide azolinium salts; protonated quaternary acrylamides; methylated quaternary polymers, such as poly [diallyl dimethylammonium chloride] and poly-[N-methyl vinyl pyridinium chloride]; and cationic guar.

Such exemplary cationic surface stabilizers and other useful cationic surface stabilizers are described in J. Cross and E. Singer, *Cationic Surfactants: Analytical and Biological Evaluation* (Marcel Dekker, 1994); P. and D. Rubingh (Editor), *Cationic Surfactants: Physical Chemistry* (Marcel Dekker, 1991); and J. Richmond, *Cationic Surfactants: Organic Chemistry*, (Marcel Dekker, 1990).

Particularly preferred nonpolymeric primary stabilizers are any nonpolymeric compound, such benzalkonium chloride, a carbonium compound, a phosphonium compound, an oxonium compound, a halonium compound, a cationic organometallic compound, a quarternary phosphorous compound, a pyridinium compound, an anilinium compound, an immonium compound, a hydroxylammonium compound, a primary ammonium compound, a secondary ammonium compound, a tertiary ammonium compound, and quarternary ammonium compounds of the formula $NR_1R_2R_3R_4^{(+)}$. For compounds of the formula $NR_1R_2R_3R_4^{(+)}$:

(i) none of $R_1$-$R_4$ are $CH_3$;
(ii) one of $R_1$-$R_4$ is $CH_3$;
(iii) three of $R_1$-$R_4$ are $CH_3$;
(iv) all of $R_1$-$R_4$ are $CH_3$;
(v) two of $R_1$-$R_4$ are $CH_3$, one of $R_1$-$R_4$ is $C_6H_5CH_2$, and one of $R_1$-$R_4$ is an alkyl chain of seven carbon atoms or less;
(vi) two of $R_1$-$R_4$ are $CH_3$, one of $R_1$-$R_4$ is $C_6H_5CH_2$, and one of $R_1$-$R_4$ is an alkyl chain of nineteen carbon atoms or more;
(vii) two of $R_1$-$R_4$ are $CH_3$ and one of $R_1$-$R_4$ is the group $C_6H_5(CH_2)_6$, where n>1;
(viii) two of $R_1$-$R_4$ are $CH_3$, one of $R_1$-$R_4$ is $C_6H_5CH_2$, and one of $R_1$-$R_4$ comprises at least one heteroatom;
(ix) two of $R_1$-$R_4$ are $CH_3$, one of $R_1$-$R_4$ is $C_6H_5CH_2$, and one of $R_1$-$R_4$ comprises at least one halogen;
(x) two of $R_1$-$R_4$ are $CH_3$, one of $R_1$-$R_4$ is $C_6H_5CH_2$, and one of $R_1$-$R_4$ comprises at least one cyclic fragment;
(xi) two of $R_1$-$R_4$ are $CH_3$ and one of $R_1$-$R_4$ is a phenyl ring; or (xii) two of $R_1$-$R_4$ are $CH_3$ and two of $R_1$-$R_4$ are purely aliphatic fragments.

Such compounds include, but are not limited to, behenalkonium chloride, benzethonium chloride, cetylpyridinium chloride, behentrimonium chloride, lauralkonium chloride, cetalkonium chloride, cetrimonium bromide, cetrimonium chloride, cethylamine hydrofluoride, chlorallylmethenamine chloride (Quaternium-15), distearyldimonium chloride (Quaternium-5), dodecyl dimethyl ethylbenzyl ammonium chloride(Quaternium-14), Quaternium-22, Quaternium-26, Quaternium-18 hectorite, dimethylaminoethylchloride hydrochloride, cysteine hydrochloride, diethanolammonium POE (10) oletyl ether phosphate, diethanolammonium POE (3)oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquaternium-1, procainehydrochloride, cocobetaine, stearalkonium bentonite, stearalkoniumhectonite, stearyl trihydroxyethyl propylenediamine dihydrofluoride, tallowtrimonium chloride, and hexadecyltrimethyl ammonium bromide.

Examples of zwitterionic stabilizers include but are not limited to proteins, phospholipids, zwitterionic polymers and zwitterionic surfactant molecules. Examples of proteins albumin, including but not limited to human serum albumin and bovine serum albumin, gelatin, casein, lysozyme. Examples of phospholipids include phosphotidylcholine, lecithin. The proteins and peptides are zwitteronic may morph into cationic or anionic depending on the pH of the medium they are exposed to. In this embodiment, it should be understood that in the considered pH range, these are molecules are zwitterionic.

Most of these surface stabilizers are known pharmaceutical excipients and are described in detail in the *Handbook of Pharmaceutical Excipients*, published jointly by the American Pharmaceutical Association and The Pharmaceutical Society of Great Britain (The Pharmaceutical Press, 5$^{th}$ ed., 2005), specifically incorporated by reference. The surface stabilizers are commercially available and/or can be prepared by techniques known in the art.

C. Flake-Like Aggregation Reducing Agent

The present invention is directed to the surprising discovery that reduction of flake-like aggregation can be achieved by adding a sugar in a nanoparticulate active agent composition or by increasing the pH level of a nanoparticulate active agent to basic conditions.

According to the present invention, the buffered formulation is at a pH that is suitably high enough to reduce flake-like aggregation. The compositions of the invention have a pH level of about pH 7.0, about 7.1, about 7.2, about 7.3, about 7.4, about 7.5, about 7.6, about 7.7, about 7.8, about 7.9, about 8.0, about 8.1, about 8.2, about 8.3, about 8.4, about 8.5, about 8.6, about 8.7, about 8.8, about 8.9, about 9.0, about 9.1, about 9.2, about 9.3, about 9.4, about 9.5, about 9.6, about 9.7, about 9.8, about 9.9, about 10.0, about 10.1, about 10.2, about 10.3, about 10.4, about 10.5, about 10.6, about 10.7, about 10.8, about 10.9, about 11.0, about 11.1, about 11.2, about 11.3, about 11.4, about 11.5, about 11.6, about 11.7, about 11.8, about 11.9, about 12.0, about 12.1, about 12.2, about 12.3, about 12.4, about 12.5, about 12.6, about 12.7, about 12.8, about 12.9, about 13.0, about 13.1, about 13.2, about 13.3, about 13.4, about 13.5, about 13.6, about 13.7, about 13.8, about 13.9, or about 14.0, or above about 14.0. In one embodiment, the pH of the formulation of the invention is in a range selected from the group consisting of pH about 9.0-about 10.0, about 10.0-about 11.0, about 11.0-about 12.0, about 12.0-about 14.0. In another embodiment, the pH of the formulation is in the range of pH about 9.5-about 11.0. In yet another embodiment, the pH of the formulation is in the range of pH about 7.0-about 9.5.

In the context of this invention, a flake-like aggregation reducing agent is defined as an agent that is capable of reducing the flake-like aggregation in a nanoparticulate active agent composition. Exemplary flake-like aggregation reducing agents include sugars, sugar alcohols and buffers. Exemplary sugars and sugar alcohols includes, but are not limited to, sucrose, fructose, glucose, erythritol, isomalt, mannitol, sorbitol, xylitol, sorbitol, and dextrose. Any pH buffering system suitable for I.V. or I.M. administration may be used, such as but not limited to a phosphate buffer, an acetate buffer or a citrate buffer. In some embodiments, the buffer is a potassium phosphate buffer, a sodium phosphate buffer, or a sodium acetate buffer.

D. Other Pharmaceutical Excipients

Pharmaceutical compositions according to the invention may also comprise one or more binding agents, filling agents, lubricating agents, suspending agents, sweeteners, flavoring agents, preservatives, buffers, wetting agents, disintegrants, effervescent agents, and other excipients. Such excipients are known in the art.

Examples of filling agents include lactose monohydrate, lactose anhydrous, and various starches; examples of binding agents include various celluloses and cross-linked polyvinylpyrrolidone, microcrystalline cellulose, such as Avicel® PH101 and Avicel® PH102, microcrystalline cellulose, and silicified microcrystalline cellulose (ProSolv SMCC™).

Suitable lubricants, including agents that act on the flowability of the powder to be compressed, may include colloidal silicon dioxide, such as Aerosil® 200, talc, stearic acid, magnesium stearate, calcium stearate, and silica gel.

Examples of sweeteners may include any natural or artificial sweetener, such as sucrose, xylitol, sodium saccharin, cyclamate, aspartame, and acesulfame. Examples of flavoring agents are Magnasweet® (trademark of MAPCO), bubble gum flavor, and fruit flavors, and the like.

Examples of preservatives include potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chloride.

Suitable diluents include pharmaceutically acceptable inert fillers, such as microcrystalline cellulose, lactose, dibasic calcium phosphate, saccharides, and/or mixtures of any of the foregoing. Examples of diluents include microcrystalline cellulose, such as Avicel® PH101 and Avicel® PH102; lactose such as lactose monohydrate, lactose anhydrous, and Pharmatose® DCL21; dibasic calcium phosphate such as Emcompress®; mannitol; starch; sorbitol; sucrose; and glucose.

Suitable disintegrants include lightly crosslinked polyvinyl pyrrolidone, corn starch, potato starch, maize starch, and modified starches, croscarmellose sodium, cross-povidone, sodium starch glycolate, and mixtures thereof.

Examples of effervescent agents include effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

E. Nanoparticulate Active Agent Particle Size

The compositions of the invention contain nanoparticulate active agent particles which have an effective average particle size of less than about 2000 nm (i.e., 2 microns). In other embodiments of the invention, the active agent particles have a size of less than about 1900 nm, less than about 1800 nm, less than about 1700 nm, less than about 1600 nm, less than about 1500 nm, less than about 1400 nm, less than about 1300 nm, less than about 1200 nm, less than about 1100 nm, less than about 1000 nm, less than about 990 nm, less than about 980 nm, less than about 970 nm, less than about 960 nm, less than about 950 nm, less than about 940 nm, less than about 930 nm, less than about 920 nm, less than about 910 nm, less than about 900 nm, less than about 890 nm, less than about 880 nm, less than about 870 nm, less than about 860 nm, less than about 850 nm, less than about 840 nm, less than about 830 nm, less than about 820 nm, less than about 810 nm, less than about 800 nm, less than about 790 nm, less than about 780 nm, less than about 770 nm, less than about 760 nm, less than about 750 nm, less than about 740 nm, less than about 730 nm, less than about 720 nm, less than about 710 nm, less than about 700 nm, less than about 690 nm, less than about 680 nm, less than about 670 nm, less than about 660 nm, less than about 650 nm, less than about 640 nm, less than about 630 nm, less than about 620 nm, less than about 610 nm, less than about 600 nm, less than about 590 nm, less than about 580 nm, less than about 570 nm, less than about 560 nm, less than about 550 nm, less than about 540 nm, less than about 530 nm, less than about 520 nm, less than about 510 nm, less than about 500 nm, less than about 490 nm, less than about 480 nm, less than about 470 nm, less than about 460 nm, less than about 450 nm, less than about 440 nm, less than about 430 nm, less than about 420 nm, less than about 410 nm, less than about 400 nm, less than about 390 nm, less than about 380 nm, less than about 370 nm, less than about 360 nm, less than about 350 nm, less than about 340 nm, less than about 330 nm, less than about 320 nm, less than about 310 nm, less than about 300 nm, less than about 290 nm, less than about 280 nm, less than about 270 nm, less than about 260 nm, less than about 250 nm, less than about 240 nm, less than about 230 nm, less than about 220 nm, less than about 210 nm, less than about 200 nm, less than about 190 nm, less than about 180 nm, less than about 170 nm, less than about 160 nm, less than about 150 nm, less than about 140 nm, less than about 130 nm, less than about 120 nm, less than about 110 nm, less than about 100, less than about 75 nm, or less than about 50 nm, as measured by light-scattering methods, microscopy, or other appropriate methods.

By "an effective average particle size of less than about 2000 nm" it is meant that at least 50% of the active agent particles have a particle size less than the effective average, by weight (or by other suitable measurement techniques, such as by volume, number, etc.), i.e., less than about 2000 nm, 1900 nm, 1800 nm, etc., when measured by the above-noted techniques. In other embodiments of the invention, at least about 60%, at least about 70%, at least about 80% at least about 90%, at least about 95%, or at least about 99% of the active agent particles have a particle size less than the effective average, i.e., less than about 2000 nm, 1900 nm, 1800 nm, etc.

In the present invention, the value for D50 of a nanoparticulate active agent composition is the particle size below which 50% of the active agent particles fall, by weight. Similarly, D90 and D99 are the particle sizes below which 90% and 99%, respectively, of the active agent particles fall, by weight (or by other suitable measurement techniques, such as by volume, number, etc.).

F. Nanoparticulate Active Agent Particulate Matter

One or more representative samplings of a particulate composition can be assayed according to the USP methods by using commercially-available particle sizing and counting machines. These commercially available particle counting machines are designed to ensure sample particulate injectable solutions comply with the USP <788> particle sizing requirements.

1. USP <788> Particulate Matter in Injections

The following text is taken from USP<788> guidelines for preparing particulate drug products for injections and Chapter 788 in its entirety is incorporated herein by reference.

This general chapter is harmonized with the corresponding texts of the European *Pharmacopoeia* and/or the *Japanese Pharmacopoeia*. These pharmacopeias have undertaken not to make any unilateral change to this harmonized chapter.

Portions of the present general chapter text that are national USP text, and therefore not part of the harmonized text, are marked with symbols (**) to specify this fact.

Particulate matter in injections and parenteral infusions consists of mobile undissolved particles, other than gas bubbles, unintentionally present in the solutions.

For the determination of particulate matter, two procedures, Method 1 (Light Obscuration Particle Count Test) and Method 2 (Microscopic Particle Count Test), are specified hereinafter. When examining injections and parenteral infusions for sub-visible particles Method 1 is preferably applied. However, it may be necessary to test some preparations by the light obscuration particle count test followed by the microscopic particle count test to reach a conclusion on conformance to the requirements.

Not all parenteral preparations can be examined for sub-visible particles by one or both of these methods. When Method 1 is not applicable, e.g. in case of preparations having reduced clarity or increased viscosity, the test should be carried out according to Method 2. Emulsions, colloids, and liposomal preparations are examples. Similarly, products that produce air or gas bubbles when drawn into the sensor may also require microscopic particle count testing. If the viscosity of the preparation to be tested is sufficiently high so as to preclude its examination by either test method, a quantitative dilution with an appropriate diluent may be made to decrease viscosity, as necessary, to allow the analysis to be performed.

The results obtained in examining a discrete unit or group of units for particulate matter cannot be extrapolated with certainty to other units that remain untested. Thus, statistically sound sampling plans must be developed if valid inferences are to be drawn from observed data to characterize the level of particulate matter in a large group of units.

Method 1. Light Obscuration Particle Count Test

Use a suitable apparatus based on the principle of light blockage which allows an automatic determination of the size of particles and the number of particles according to size. The definition for particle-free water is provided in Reagent Specifications under Reagents, Indicators and Solution section.

The apparatus is calibrated using dispersions of spherical particles of known sizes between 10 μm and 25 μm. These standard particles are dispersed in particle-free water.

Care must be taken to avoid aggregation of particles during dispersion. System suitability can be verified by using the USP Particle Count RS (<11>).

General Precautions

The test is carried out under conditions limiting particulate matter, preferably in a laminar-flow cabinet.

Very carefully wash the glassware and filtration equipment used, except for the membrane filters, with a warm detergent solution and rinse with abundant amounts of water to remove all traces of detergent. Immediately before use, rinse the equipment from top to bottom, outside and then inside, with particle-free water.

Take care not to introduce air bubbles into the preparation to be examined, especially when fractions of the preparation are being transferred to the container in which the determination is to be carried out.

To check that the environment is suitable for the test, that the glassware is properly cleaned and that the water to be used is particle-free, the following test is carried out: determine the particulate matter in 5 samples of particle-free water, each of 5 ml, according to the method described below. If the number of particles of 10 μm or greater size exceeds 25 for the combined 25 ml, the precautions taken for the test are not sufficient. The preparatory steps must be repeated until the environment, glassware and water are suitable for the test.

Method

Mix the contents of the sample by slowly inverting the container 20 times successively. If necessary, cautiously remove the sealing closure. Clean the outer surfaces of the container opening using a jet of particle-free water and remove the closure, avoiding any contamination of the contents. Eliminate gas bubbles by appropriate measures such as allowing to stand for 2 min or sonicating.

For large-volume parenterals, single units are tested. For small-volume parenterals less than 25 ml in volume, the contents of 10 or more units is combined in a cleaned container to obtain a volume of not less than 25 ml; the test solution may be prepared by mixing the contents of a suitable number of vials and diluting to 25 ml with particle-free water or with an appropriate particle-free solvent when particle-free water is not suitable. Small-volume parenterals having a volume of 25 ml or more may be tested individually.

Powders for parenteral use are reconstituted with particle-free water or with an appropriate particle-free solvent when particle-free water is not suitable.

The number of test specimens must be adequate to provide a statistically sound assessment. For large-volume parenterals or for small-volume parenterals having a volume of 25 ml or more, fewer than 10 units may be tested, based on an appropriate sampling plan.

Remove four portions, each of not less than 5 ml, and count the number of particles equal to or greater than 10 μm and 25 μm. Disregard the result obtained for the first portion, and calculate the mean number of particles for the preparation to be examined.

Evaluation

For preparations supplied in containers with a nominal volume of more than 100 ml, apply the criteria of test 1.A.

For preparations supplied in containers with a nominal volume of less than 100 ml, apply the criteria of test 1.B.

For preparations supplied in containers with a nominal volume of 100 ml, apply the criteria of test 1.B [Note: Test 1.A is used in the Japanese Pharmacopoeia]

If the average number of particles exceeds the limits, test the preparation by the Microscopic Particle Count Test.

Test 1.A—Solutions for parenteral infusion or solutions for injection supplied in containers with a nominal content of more than 100 mL.

The preparation complies with the test if the average number of particles present in the units tested does not exceed 25 per mL equal to or greater than 10 μm and does not exceed 3 per mL equal to or greater than 25 μm.

Test 1.B—Solutions for parenteral infusion or solutions for injection supplied in containers with a nominal content of less than 100 ml.

The preparation complies with the test if the average number of particles present in the units tested does not exceed 6000 per container equal to or greater than 10 μm and does not exceed 600 per container equal to or greater than 25 μm.

Method 2. Microscopic Particle Count Test

Use a suitable binocular microscope, filter assembly for retaining particulate matter and membrane filter for examination.

The microscope is equipped with an ocular micrometer calibrated with an objective micrometer, a mechanical stage capable of holding and traversing the entire filtration area of the membrane filter, two suitable illuminators to provide episcopic illumination in addition to oblique illumination, and is adjusted to 100±10 magnifications.

The ocular micrometer is a circular diameter graticule (see FIG. 1) and consists of a large circle divided by crosshairs into quadrants, transparent and black reference circles 10 μm and 25 μm in diameter at 100 magnifications, and a linear scale graduated in 10 μm increments. It is calibrated using a stage micrometer that is certified by either a domestic or international standard institution. A relative error of the linear scale of the graticule within ±2 percent is acceptable. The large circle is designated the graticule field of view (GFOV).

Two illuminators are required. One is an episcopic bright-field illuminator internal to the microscope, the other is an external, focusable auxiliary illuminator adjustable to give reflected oblique illumination at an angle of 10° to 20°.

The filter assembly for retaining particulate matter consists of a filter holder made of glass or other suitable material, and is equipped with a vacuum source and a suitable membrane filter.

The membrane filter is of suitable size, black or dark gray in color, non-gridded or gridded, and 1.0 μm or finer in nominal pore size.

General Precautions

The test is carried out under conditions limiting particulate matter, preferably in a laminar-flow cabinet.

Very carefully wash the glassware and filter assembly used, except for the membrane filter, with a warm detergent solution and rinse with abundant amounts of water to remove all traces of detergent. Immediately before use, rinse both sides of the membrane filter and the equipment from top to bottom, outside and then inside, with particle-free water.

In order to check that the environment is suitable for the test, that the glassware and the membrane filter are properly cleaned and that the water to be used is particle-free, the following test is carried out: determine the particulate matter of a 50 ml volume of particle-free water according to the method described below. If more than 20 particles 10 μm or larger in size or if more than 5 particles 25 µm or larger in size are present within the filtration area, the precautions taken for the test are not sufficient. The preparatory steps must be repeated until the environment, glassware, membrane filter and water are suitable for the test.

2. USP <788> as Applied to the Invention

The present invention is not limited to the specific instruments or strategies outlined in USP<788> for obtaining an approved particulate drug product. For instance, the skilled person knows that various aspects of the USP<788>"Microscopy" method can vary, such as the size of the pores of a filter, the source and direction of light illumination, the type of color filter used to help visualize the particles with the microscope, and the various different ways one can reduce the viscosity of a solution by dilution. For instance, the skilled person knows that the filter may have a filter pore size of about 5 µm in size, about 4 µm in size, about 3 µm in size, about 2 µm in size, or about 1 µm in size. In one embodiment, the filter pore size is about from 1-5 µm in size. Similarly, the skilled person knows that the microscopy platform onto which the sample is viewed may be illuminated from the top or bottom of the microscopy apparatus. In one embodiment, the source of light illumination is from the top. Likewise, the skilled person knows that it is possible to change the color filter used to visualize the sample depending on the source and direction of the illumination. Thus, the skilled person knows of the availability of dark, black, grey, or white filters for this purpose. In one embodiment, the filter is white. Thus, in one embodiment, the present invention contemplates obtaining a particulate drug product that complies with the USP<788> size threshold requirements by using a filter that has a 5 µm pore size, illuminated from the top using a white color filter. In another embodiment, the skilled person knows how to dilute a solution to reduce viscosity in the USP<788> methods.

The skilled person would be able to determine the optimal or suitable conditions for retaining the nanoparticulate active agent in a non-aggregated form, so that the formulation complies with USP<788>. Thus, nanoparticulate active agent compositions of the present invention described herein contains (i) no more than 6,000 particles that are greater than 10 µm in size and (ii) no more than 600 particles that are greater than 25 µm in size, under the Light Obscuration test of USP<788>. And in another embodiment, the nanoparticulate active agent compositions of the present invention contains no more than (i) 3,000 particles that are greater than 10 µm in size and (ii) no more than 300 particles that are greater than 25 µm in size, under use of the Microscopy method of USP<788>.

The present invention is not limited to the particular size thresholds set forth in USP<788>. Thus in one embodiment, an injectable formulation of the present invention has fewer than about 1000 particles larger than 25 µm, fewer than about 900 particles larger than 25 µm, fewer than about 800 particles larger than 25 µm, fewer than about 700 particles larger than 25 µm, fewer than about 600 particles larger than 25 µm, fewer than about 500 particles larger than 25 µm, fewer than about 400 particles larger than 25 µm, fewer than about 300 particles larger than 25 µm, fewer than about 200 particles larger than 25 µm, fewer than about 150 particles larger than 25 µm, fewer than about 100 particles larger than 25 µm, or fewer than about 50 particles larger than 25 µm.

In another embodiment, an injectable formulation of the present invention has fewer than about 10000 particles larger than 10 µm, fewer than about 9000 particles larger than 10 µm, fewer than about 8000 particles larger than 10 µm, fewer than about 7000 particles larger than 10 µm, fewer than about 6000 particles larger than 10 µm, fewer than about 5000 particles larger than 10 µm, fewer than about 4000 particles larger than 10 µm, fewer than about 3000 particles larger than 10 µm, fewer than about 2000 particles larger than 10 µm, fewer than about 1000 particles larger than 10 µm, fewer than about 900 particles larger than 10 µm, fewer than about 800 particles larger than 10 µm, fewer than about 700 particles larger than 10 µm, fewer than about 600 particles larger than 10 µm, fewer than about 500 particles larger than 10 µm, fewer than about 400 particles larger than 10 µm, fewer than about 300 particles larger than 10 µm, fewer than about 200 particles larger than 10 µm, fewer than about 175 particles larger than 10 µm, fewer than about 150 particles larger than 10 µm, fewer than about 100 particles larger than 10 µm, fewer than about 75 particles larger than 10 µm, fewer than about 50 particles larger than 10 µm, fewer than about 25 particles larger than 10 µm, fewer than about 15 particles larger than 10 µm, fewer than about 10 particles larger than 10 µm, fewer than about 5 particles larger than 10 µm, fewer than about 3 particles larger than 10 µm, or essentially no particles larger than 10 µm.

G. Concentration of Nanoparticulate Active Agent, Surface Stabilizer, and Flake-Like Aggregation Reducing Agent The relative amounts of active agent, surface stabilizer and flake-like aggregation reducing agent can vary widely. The optimal amount of the individual components can depend, for example, upon the particular active agent and surface stabilizer selected, the hydrophilic lipophilic balance (HLB), melting point, and the surface tension of water solutions of the surface stabilizer, etc.

The concentration of the surface stabilizer can vary from about 0.5% to about 99.999%, from about 5.0% to about 99.9%, or from about 10% to about 99.5%, by weight, based on the total combined dry weight of the at least one active agent and at least one surface stabilizer, not including other excipients.

The concentration of the at least one active agent can vary from about 99.5% to about 0.001%, from about 95% to about 0.1%, or from about 90% to about 0.5%, by weight, based on the total combined dry weight of the active agent and at least one surface stabilizer, not including other excipients.

III. Methods of Making Nanoparticulate Active Agent Formulations

The nanoparticulate active agent compositions of the invention, comprising at least one surface stabilizer and at least one flake-like aggregation reducing agent, can be made using, for example, milling or attrition (including but not limited to wet milling), homogenization, precipitation, freezing, template emulsion techniques, supercritical fluid techniques, nano-electrospray techniques, or any combination thereof. Exemplary methods of making nanoparticulate active agent compositions are described in the '684 patent. Methods of making nanoparticulate active agent compositions are also described in U.S. Pat. No. 5,518,187 for "Method of Grinding Pharmaceutical Substances;" U.S. Pat. No. 5,718,388 for "Continuous Method of Grinding Pharmaceutical Substances;" U.S. Pat. No. 5,862,999 for "Method of Grinding Pharmaceutical Substances;" U.S. Pat. No. 5,665,331 for "Co-Microprecipitation of Nanoparticulate Pharmaceutical Agents with Crystal Growth Modifiers;" U.S. Pat. No. 5,662,883 for "Co-Microprecipitation of Nanoparticulate Pharmaceutical Agents with Crystal Growth Modifiers;" U.S. Pat. No. 5,560,932 for "Microprecipitation of Nanoparticulate Pharmaceutical Agents;" U.S. Pat. No. 5,543,133 for "Process of Preparing X-Ray Contrast Compositions Containing Nanoparticles;" U.S. Pat. No. 5,534,270 for "Method of Preparing Stable Drug Nanoparticles;" U.S. Pat. No. 5,510,118 for "Process of Preparing Therapeutic Compositions Containing Nanoparticles;" and U.S. Pat. No. 5,470,583 for "Method of Preparing Nanoparticle Compositions Containing Charged Phospholipids to Reduce Aggregation," all of which are specifically incorporated by reference.

A. Milling to Obtain Nanoparticulate Active Agent Dispersions

Milling the active agent to obtain a nanoparticulate colloidal dispersion comprises dispersing active agent particles in a liquid dispersion media in which the active agent is poorly soluble, followed by applying mechanical means in the presence of grinding media to reduce the particle size of the active agent to the desired effective average particle size. The dispersion media can be, for example, water, safflower oil, ethanol, t-butanol, glycerin, polyethylene glycol (PEG), hexane, or glycol. Water is a preferred dispersion media.

The active agent particles are preferably reduced in size in the presence of at least one surface stabilizer. Alternatively, the active agent particles can be contacted with at least one surface stabilizer either during or after attrition. One or more flake-like aggregation reducing agent may be added before, during, or after attrition. Other compounds, such as a diluent, can be added to the composition before, during, or after the size reduction process. Dispersions can be manufactured continuously or in a batch mode.

The grinding media can comprise particles that are preferably substantially spherical in shape, e.g., beads, consisting essentially of polymeric or copolymeric resin. Alternatively, the grinding media can comprise a core having a coating of a polymeric or copolymeric resin adhered thereon.

In general, suitable polymeric or copolymeric resins are chemically and physically inert, substantially free of metals, solvent, and monomers, and of sufficient hardness and friability to enable them to avoid being chipped or crushed during grinding. Suitable polymeric or copolymeric resins include crosslinked polystyrenes, such as polystyrene crosslinked with divinylbenzene; styrene copolymers; polycarbonates; polyacetals, such as Delrin™ (E.I. du Pont de Nemours and Co.); vinyl chloride polymers and copolymers; polyurethanes; polyamides; poly(tetrafluoroethylenes), e.g., Teflon® (E.I. du Pont de Nemours and Co.), and other fluoropolymers; high density polyethylenes; polypropylenes; cellulose ethers and esters such as cellulose acetate; polyhydroxymethacrylate; polyhydroxyethyl acrylate; and silicone-containing polymers such as polysiloxanes and the like. The polymer can be biodegradable. Exemplary biodegradable polymers or copolymers include poly(lactides), poly(glycolide) copolymers of lactides and glycolide, polyanhydrides, poly(hydroxyethyl methacrylate), poly(imino carbonates), poly(N-acylhydroxyproline)esters, poly(N-palmitoyl hydroxyproline) esters, ethylene-vinyl acetate copolymers, poly(orthoesters), poly(caprolactones), and poly(phosphazenes). For biodegradable polymers or copolymers, contamination from the media itself advantageously can metabolize in vivo into biologically acceptable products that can be eliminated from the body.

The grinding media preferably ranges in size from about 0.01 to about 3 mm. For fine grinding, the grinding media is preferably from about 0.02 to about 2 mm, and more preferably from about 0.03 to about 1 mm in size.

The polymeric or copolymeric resin can have a density from about 0.8 to about 3.0 g/cm³.

In a preferred grinding process the active agent particles are made continuously. Such a method comprises continuously introducing an active agent composition according to the invention into a milling chamber, contacting the active agent composition according to the invention with grinding media while in the chamber to reduce the active agent particle size of the composition according to the invention, and continuously removing the nanoparticulate active agent composition from the milling chamber.

The grinding media is separated from the milled nanoparticulate active agent composition according to the invention using conventional separation techniques, in a secondary process such as by simple filtration, sieving through a mesh filter or screen, and the like. Other separation techniques such as centrifugation may also be employed.

B. Precipitation to Obtain Nanoparticulate Active Agent Compositions

Another method of forming the desired nanoparticulate active agent composition is by microprecipitation. This is a method of preparing stable nanoparticulate active agent dispersions of poorly soluble active agents in the presence of one or more surface stabilizers and one or more colloid stability enhancing surface active agents free of any trace toxic solvents or solubilized heavy metal impurities. Such a method comprises, for example: (1) dissolving the poorly soluble active agent in a suitable solvent; (2) adding the formulation from step (1) to a solution comprising at least one surface stabilizer and optionally one or more flake-like aggregation reducing agent, to form a clear solution; and (3) precipitating the formulation from step (2) using an appropriate non-solvent. The method can be followed by removal of any formed salt, if present, by dialysis or diafiltration and concentration of the dispersion by conventional means.

C. Homogenization to Obtain Nanoparticulate Active Agent Compositions

Exemplary homogenization methods of preparing active agent nanoparticulate active agent compositions are described in U.S. Pat. No. 5,510,118, for "Process of Preparing Therapeutic Compositions Containing Nanoparticles."

Such a method comprises dispersing active agent particles in a liquid dispersion media in which the active agent is poorly soluble, followed by subjecting the dispersion to homogenization to reduce the particle size of the active agent to the desired effective average particle size. The active agent particles can be reduced in size in the presence of at least one surface stabilizer and, optionally, one or more flake-like aggregation reducing agent. Alternatively, the active agent particles can be contacted with at least one surface stabilizer and one or more flake-like aggregation reducing agent either during or after attrition. Other compounds, such as a diluent, can be added to the composition either before, during, or after the size reduction process. Dispersions can be manufactured continuously or in a batch mode.

D. Cryogenic Methodologies to Obtain Nanoparticulate Active Agent Compositions

Another method of forming the desired nanoparticulate active agent composition is by spray freezing into liquid (SFL). This technology comprises an organic or organo-aqueous solution of an active agent with one or more surface stabilizers. One or more flake-like aggregation reducing agent can be added either before, during, or after particle size reduction. The composition is injected into a cryogenic liquid, such as liquid nitrogen. The droplets of active agent solution freeze at a rate sufficient to minimize crystallization and particle growth, thus formulating nanostructured active agent particles. Depending on the choice of solvent system and processing conditions, the nanoparticulate active agent particles can have varying particle morphology. In the isolation step, the nitrogen and solvent are removed under conditions that avoid agglomeration or ripening of the active agent particles.

As a complementary technology to SFL, ultra rapid freezing (URF) may also be used to created equivalent nanostructured active agent particles with greatly enhanced surface area. URF comprises an organic or organoaqueous solution of active agent with stabilizers onto a cryogenic substrate.

E. Emulsion Methodologies to Obtain Nanoparticulate Active Agent Compositions

Another method of forming the desired nanoparticulate active agent composition is by template emulsion. Template emulsion creates nanostructured active agent particles with controlled particle size distribution and rapid dissolution performance. The method comprises an oil-in-water emulsion that is prepared, then swelled with a non-aqueous solution comprising active agent and one or more surface stabilizers. One or more flake-like aggregation reducing agent can be added either before, during, or after particle size reduction. The particle size distribution of the active agent is a direct result of the size of the emulsion droplets prior to loading with the active agent, a property which can be controlled and optimized in this process. Furthermore, through selected use of solvents and stabilizers, emulsion stability is achieved with no or suppressed Ostwald ripening. Subsequently, the solvent and water are removed, and the stabilized nanostructured active agent particles are recovered. Various active agent particle morphologies can be achieved by appropriate control of processing conditions.

F. Supercritical Fluid Methods of Making Active Agent Nanoparticles

Nanoparticulate active agent compositions can also be made in methods utilizing supercritical fluids. In such a method, the active agent is dissolved in a solution or vehicle which can also contain at least one surface stabilizer. One or more flake-like aggregation reducing agent can be added either before, during, or after particle size reduction. The solution and a supercritical fluid are then co-introduced into a particle formation vessel. If a surface stabilizer was not previously added to the vehicle, it can be added to the particle formation vessel The temperature and pressure are controlled, such that dispersion and extraction of the vehicle occur substantially simultaneously by the action of the supercritical fluid. Chemicals described as being useful as supercritical fluids include carbon dioxide, nitrous oxide, sulphur hexafluoride, xenon, ethylene, chlorotrifluoromethane, ethane, and trifluoromethane.

Examples of known supercritical methods of making nanoparticles include International Patent Application No. WO 97/14407 to Pace et al., published on Apr. 24, 1997, which refers to particles of water insoluble biologically active compounds with an average size of 100 nm to 300 nm prepared by dissolving the compound in a solution and then spraying the solution into compressed gas, liquid, or supercritical fluid in the presence of appropriate surface stabilizers.

Similarly, U.S. Pat. No. 6,406,718 to Cooper et al. describes a method for forming a particulate fluticasone propionate product comprising the co-introduction of a supercritical fluid and a vehicle containing at least fluticasone propionate in solution or suspension into a particle formation vessel, the temperature and pressure in which are controlled, such that dispersion and extraction of the vehicle occur substantially simultaneously by the action of the supercritical fluid. Chemicals described as being useful as supercritical fluids include carbon dioxide, nitrous oxide, sulphur hexafluoride, xenon, ethylene, chlorotrifluoromethane, ethane, and trifluoromethane. The supercritical fluid may optionally contain one or more modifiers, such as methanol, ethanol, ethyl acetate, acetone, acetonitrile or any mixture thereof. A supercritical fluid modifier (or co-solvent) is a chemical which, when added to a supercritical fluid, changes the intrinsic properties of the supercritical fluid in or around the critical point. According to Cooper et al., the fluticasone propionate particles produced using supercritical fluids have a particle size range of 1 to 10 microns, preferably 1 to 5 microns.

G. Nano-Electrospray Techniques Used to Obtain Nanoparticulate Active Agent Compositions In electrospray ionization a liquid is pushed through a very small charged, usually metal, capillary. This liquid contains the desired active agent dissolved in a large amount of solvent, which is usually much more volatile than the active agent (e.g., analyte). Volatile acids, bases or buffers are often added to this solution as well. The analyte exists as an ion in solution either in a protonated form or as an anion. As like charges repel, the liquid pushes itself out of the capillary and forms a mist or an aerosol of small droplets about 10 µm across. This jet of aerosol droplets is at least partially produced by a process involving the formation of a Taylor cone and a jet from the tip of this cone. A neutral carrier gas, such as nitrogen gas, is sometimes used to help nebulize the liquid and to help evaporate the neutral solvent in the small droplets. As the small droplets evaporate, suspended in the air, the charged analyte molecules are forced closer together. The drops become unstable as the similarly charged molecules come closer together and the droplets once again break up. This is referred to as Coulombic fission because it is the repulsive Coulombic forces between charged analyte molecules that drive it. This process repeats itself until the analyte is free of solvent and is a lone ion.

In nanotechnology the electrospray method may be employed to deposit single active agent particles on surfaces. This is accomplished by spraying colloids and ensuring that on average there is not more than one particle per droplet. Consequent drying of the surrounding solvent results in an aerosol stream of single active agent particles. Here the ionizing property of the process is not crucial for the application but may be put to use in electrostatic precipitation of the particles.

IV. Methods of Using Nanoparticulate Active Agent Formulations

The nanoparticulate active agent compositions of the present invention can be administered to humans and animals via any conventional means including, but not limited to, orally, rectally, ocularly, parenterally (intravenous, intramuscular, or subcutaneous), intracisternally, pulmonary, intravaginally, intraperitoneally, locally (powders, ointments or drops), or as a buccal or nasal spray.

Compositions suitable for parenteral injection may comprise physiologically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents, or vehicles including water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

The nanoparticulate active agent compositions may also contain adjuvants such as preserving, wetting, emulsifying, and dispensing agents. Prevention of the growth of microorganisms can be ensured by various antibacterial and antifungal agents, such as parabens, chlorobutanol, phenol, sorbic acid, and the like. It may also be desirable to include isotonic agents, such as sugars, sodium chloride, and the like. Prolonged absorption of the injectable pharmaceutical form can be brought about by the use of agents delaying absorption, such as aluminum monostearate and gelatin.

Solid dosage forms for oral administration include capsules, tablets, pills, powders, and granules. In such solid dosage forms, the active agent is admixed with at least one of the following: (a) one or more inert excipients (or carrier), such as sodium citrate or dicalcium phosphate; (b) fillers or extenders, such as starches, lactose, sucrose, glucose, mannitol, and silicic acid; (c) binders, such as carboxymethylcellulose, alignates, gelatin, polyvinylpyrrolidone, sucrose and acacia; (d) humectants, such as glycerol; (e) disintegrating agents, such as agar-agar, calcium carbonate, potato or tapioca starch, alginic acid, certain complex silicates, and sodium carbonate; (f) solution retarders, such as paraffin; (g) absorption accelerators, such as quaternary ammonium compounds; (h) wetting agents, such as cetyl alcohol and glycerol monostearate; (i) adsorbents, such as kaolin and bentonite; and (j) lubricants, such as talc, calcium stearate, magnesium stearate, solid polyethylene glycols, sodium lauryl sulfate, or mixtures thereof. For capsules, tablets, and pills, the dosage forms may also comprise buffering agents.

Liquid dosage forms for oral administration include pharmaceutically acceptable emulsions, solutions, suspensions, syrups, and elixirs. In addition to the active agent, the liquid dosage forms may comprise inert diluents commonly used in the art, such as water or other solvents, solubilizing agents, and emulsifiers. Exemplary emulsifiers are ethyl alcohol, isopropyl alcohol, ethyl carbonate, ethyl acetate, benzyl alcohol, benzyl benzoate, propyleneglycol, 1,3-butyleneglycol, dimethylformamide, oils, such as cottonseed oil, groundnut oil, corn germ oil, olive oil, castor oil, and sesame oil, glycerol, tetrahydrofurfuryl alcohol, polyethyleneglycols, fatty acid esters of sorbitan, or mixtures of these substances, and the like.

Besides such inert diluents, the composition can also include adjuvants, such as wetting agents, emulsifying and suspending agents, sweetening, flavoring, and perfuming agents.

Actual dosage levels of active agent in the nanoparticulate compositions of the invention may be varied to obtain an amount of active agent that is effective to obtain a desired therapeutic response for a particular composition and method of administration. The selected dosage level therefore depends upon the desired therapeutic effect, the route of administration, the potency of the administered active agent, the desired duration of treatment, and other factors.

Dosage unit compositions may contain such amounts of such submultiples thereof as may be used to make up the daily dose. It will be understood, however, that the specific dose level for any particular patient will depend upon a variety of factors including the body weight, general health, sex, diet, time and route of administration, potency of the administered active agent, rates of absorption and excretion, combination with other active agents, and the severity of the particular disease being treated.

The following examples are given to illustrate the present invention. It should be understood, however, that the invention is not to be limited to the specific conditions or details described in these examples. Throughout the specification, any and all references to a publicly available document, including a U.S. patent, are specifically incorporated by reference.

The formulations in the examples that follow were also investigated using a light microscope. Here, "stable" nanoparticulate dispersions (uniform Brownian motion) were readily distinguishable from "aggregated" dispersions (relatively large, nonuniform particles without motion).

Example 1

The purpose of this example was to prepare a nanoparticulate meloxicam dispersion suitable for injection that met the USP <788> standard and test the stability of the dispersion.

A slurry of 20% (w/w) meloxicam (supplied by anonima Materie Sintetiche E Affini Spa) and 4% (w/w) polyvinyl pyrrolidone (Povidone Kollidon® 17 PF) was milled for 4 hours in a NanoMill-2 system using PolyMill® 500 μm grinding media. The meloxicam particle size stability under controlled conditions was monitored over time.

It was observed that under all stability conditions, the nanopartiuclate meloxicam dispersion prepared as described above had levels of flake-like particulates that were too numerous to count and consequently failed to meet USP<788> criteria. FIG. 1 shows the particulates found in the NCD™.

Example 2

The purpose of this example was to screen nanoparticulate meloxicam formulations for the stability of particle size and particulate matter.

The nanoparticulate meloxicam formulations as outlined in FIGS. 2-6 and further summarized in Table 1 below were made as described in Example 1. The resulting dispersions were tested at 5° C., 25° C. or 40° C. for up to 3 months.

TABLE 1

| Formulation | Storage time Days | Condition ° C. | Dmean nm | D50 nm | D90 nm |
|---|---|---|---|---|---|
| 2.5% meloxicam, 0.5% Pvp K17 | 30 | 25 | 157 | 95 | 334 |
|  | 30 | 40 | 295 | 259 | 476 |
| 2.5% meloxicam, 0.5% Pvp K17, 0.25% NaDOC | 60 | 5 | 99 | 89 | 121 |
|  | 60 | 25 | 101 | 90 | 127 |
|  | 60 | 40 | 106 | 91 | 145 |

TABLE 1-continued

| Formulation | Storage time Days | Condition ° C. | Dmean nm | D50 nm | D90 nm |
|---|---|---|---|---|---|
| 2.5% meloxicam, 0.25% Pvp K17, 0.25% Tween 80 | 29 | 5 | 273 | 256 | 417 |
| | 29 | 25 | 468 | 446 | 710 |
| | 29 | 40 | 585 | 566 | 858 |
| 2.5% meloxicam, 0.5% Pvp K12, 0.25% NaDOC | 62 | 5 | 102 | 89 | 130 |
| | 62 | 25 | 104 | 91 | 137 |
| | 62 | 40 | 106 | 91 | 148 |
| 2.5% meloxicam, 0.5% Tween 20, 0.5% Span 20 | 29 | 5 | 113 | 89 | 225 |
| | 29 | 25 | 451 | 425 | 696 |
| | 29 | 40 | 548 | 537 | 825 |
| 2.3% meloxicam, 0.5% Pvp K17, 2.3% PEG400, 0.23% NaDOC | 0 | NA | 123 | 105 | 214 |
| 2.5% meloxicam, 0.5% Pvp K17, 0.25% NaDOC, 200 mM Sodium Phosphate pH 9 | 7 | 5 | 139 | | |
| 2.5% meloxicam, 0.5% Pvp K17, 0.125% NaDOC, 125 mM Sodium Phosphate pH 7.5 | 14 | 5 | 139 | | |
| 2.3% meloxicam, 0.46% Pvp K17, 0.23% NaDOC, 50 mM Sodium Phosphate pH 6 | 7 | 5 | 102 | | |
| 2.7% meloxicam, 0.54% Pvp K17, 200 mM Sodium Phosphate pH 9 | 14 | 5 | 164 | | |
| 2.5% meloxicam, 0.5% Pvp K17, 0.08% NaDOC, 0.1M Potassium Phosphate pH 7.5 | 0 | 5 | 115 | | |
| 3.4% meloxicam, 0.68% Pvp K17, 0.23% NaDOC, 0.68% Tween 80, 100 mM Sodium Phosphate pH 8 | 0 | 5 | 220 | | |

Table 2 summarizes the aforementioned formulations and the levels of particulate matter. This table shows a need for further improvement in some of formulations to reduce the flake-like particulates.

TABLE 2

| Formulation | Storage time Days | Storage Condition ° C. | Particles Observed (100 GFOV)* | Approx. Particles Retained on 47 mm Filter |
|---|---|---|---|---|
| 2.5% meloxicam, 0.5% Pvp K17, 0.125% NaDOC | 7 | 5 | 575 | 9,976 |
| | 7 | 25 | 127 | 2,203 |
| | 7 | 40 | 477 | 8,275 |
| 2.5% meloxicam, 0.38% Pvp K17, 0.19% NaDOC | 7 | 5 | 1,096 | 19,015 |
| | 7 | 25 | 5 | 87 |
| | 7 | 40 | 224 | 3,886 |
| 2.5% meloxicam, 0.5% Pvp K17, 0.375% NaDOC | 7 | 5 | 118 | 2,047 |
| | 7 | 25 | 78 | 1,353 |
| | 7 | 40 | TNTC | N/A |
| 2.5% meloxicam, 0.38% Pvp K17, 0.38% NaDOC | 7 | 5 | 70 | 1,214 |
| | 7 | 25 | 45 | 781 |
| | 7 | 40 | 182 | 3,158 |
| 2.5% meloxicam, 0.75% Pvp K17, 0.125% NaDOC | 0 | NA | 291 | 2019 |
| 2.5% meloxicam, 0.75% Pvp K17, 0.25% NaDOC | 7 | 5 | 242 | 4,198 |
| | 7 | 25 | 8 | 139 |
| | 7 | 40 | 72 | 1,249 |
| 2.5% meloxicam, 0.75% Pvp K17, 0.5% NaDOC | 7 | 25 | 20 | 347 |
| 2.5% meloxicam, 0.5% Pvp K12, 0.125% NaDOC | 7 | 5 | 168 | 2,915 |
| | 7 | 25 | 292 | 5,066 |
| | 7 | 40 | 199 | 3,452 |
| 2.5% meloxicam, 0.5% Pvp K12, 0.25% NaDOC | 7 | 5 | 94 | 1,631 |
| | 7 | 25 | 68 | 1,180 |
| | 7 | 40 | 368 | 6,384 |
| 2.5% meloxicam, 0.5% Pvp K12, 0.375% NaDOC | 7 | 5 | 58 | 1,006 |
| | 7 | 25 | 98 | 1700 |
| | 7 | 40 | 786 | |
| 2.5% meloxicam, 0.5% Pvp K17, 0.5% NaDOC | 7 | 5 | 18 | 312 |
| | 7 | 25 | 65 | 1,128 |
| | 7 | 40 | 71 | 1,232 |
| 2.5% meloxicam, 0.75% Pvp K17, 0.125% NaDOC | 7 | 5 | 27 | 468 |
| | 7 | 40 | 471 | 8171 |
| 2.5% meloxicam, 0.75% Pvp K2, 0.25% NaDOC | 7 | 5 | 23 | 399 |
| | 7 | 25 | 385 | 6,679 |
| | 7 | 40 | 33 | 573 |
| 2.5% meloxicam, 0.75% Pvp K12, 0.375% NaDOC | 7 | 25 | 89 | 1,544 |
| 2.5% meloxicam, 0.75% Pvp K12, 0.5% NaDOC | 0 | NA | 41 | 711 |
| 2.3% meloxicam, 0.5% Pvp K17, 2.3% PEG400, 0.23% NaDOC | 0 | NA | could not filter | |

TABLE 2-continued

| Formulation | Storage time Days | Storage Condition °C. | Particles Observed (100 GFOV)* | Approx. Particles Retained on 47 mm Filter |
|---|---|---|---|---|
| 2.5% meloxicam, 0.5% Pvp K17, 0.25% NaDOC, 5% Sucrose | 7 | 5 | 2 | 35 |
| | 7 | 25 | 6 | 104 |
| | 7 | 40 | 0 | 0 |
| 2.5% meloxicam, 0.5% Pvp K17, 0.25% NaDOC, 200 mM Sodium Phosphate pH 9 | 7 | 5 | | 107 |
| 2.5% meloxicam, 0.5% Pvp K17, 0.125% NaDOC, 125 mM Sodium Phosphate pH 7.5 | 14 | 5 | | 7165 |
| 2.3% meloxicam, 0.46% Pvp K17, 0.23% NaDOC, 50 mM Sodium Phosphate pH 6 | 7 | 5 | | 103 |
| 2.7% meloxicam, 0.54% Pvp K17, 200 mM Sodium Phosphate pH 9 | 14 | 5 | | 1145 |
| 2.5% meloxicam, 0.5% Pvp K17, 0.08% NaDOC, 0.1M Potassium Phosphate pH 7.5 | 14 | 5 | | 698 |
| 3.4% meloxicam, 0.68% Pvp K17, 0.23% NaDOC, 0.68% Tween 80, 100 mM Sodium Phosphate pH 8 | 7 | 5 | | 1694 |

Certain formulations in Table 2, such as the one formulation containing sucrose and ones that were pH adjusted with pH buffers show significant improvement in particulate matter levels Example 3

The purpose of this example was to test the stability of a nanoparticulate meloxicam formulation comprising mannitol in terms of meloxicam particle size and particulate matter.

A slurry of 10% (w/w) meloxicam, 2.5% (w/w) PVP K17, 0.75% (w/w) NaDOC and 10% (w/w) mannitol in polymill 500 μm grinding media at 89% media load was milled for 4 hours using a DynoMill 300 mL chamber in recirculation mode to obtain a nanopartiuclate dispersion of meloxicam. The nanoparticulate meloxicam dispersion was diluted to 5% meloxicam, 1.25% PVP K17, 0.375% NaDOC, 5% mannitol and 15% sucrose with a 30% sucrose solution. The formulation was stored at 5° C. for 3 months and tested for particulate matter.

Figure 7:
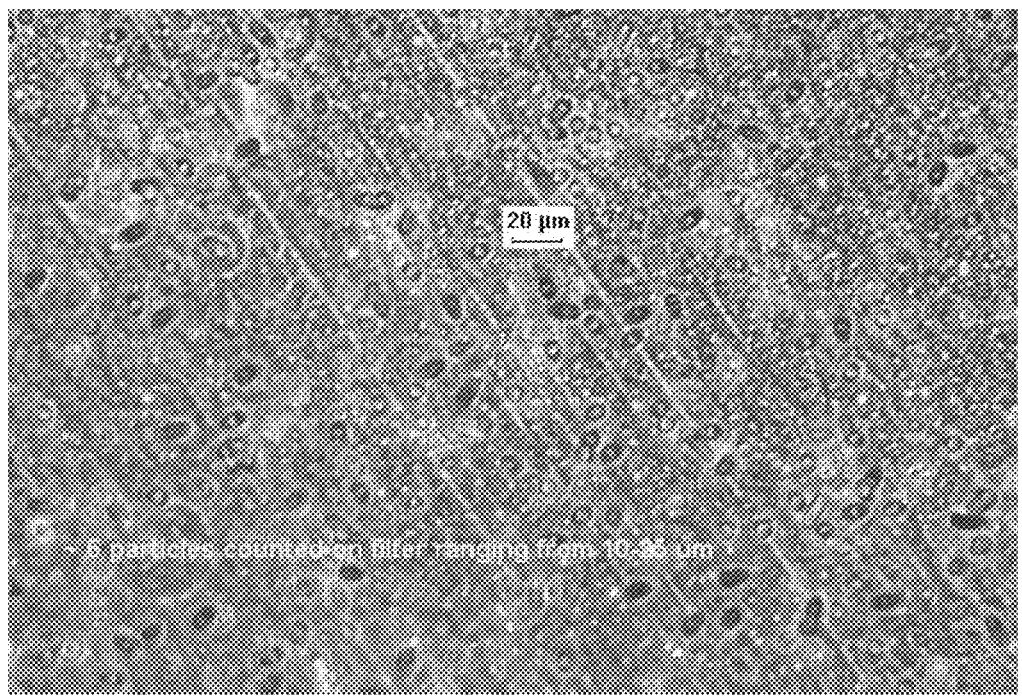
FIG. 7 shows a magnified image of the NCD™ comprising 5% mannitol and 15% sucrose after it was filtered through an 8 μm filter at 200× magnification.
Figure 8A:
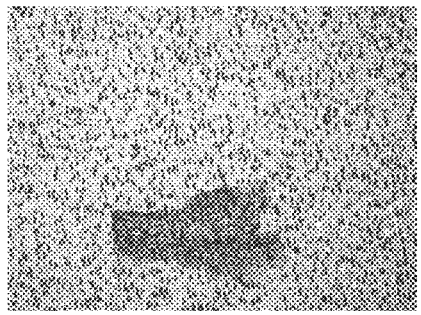
FIGS. 8A-8B show the images of an NCD™ formulation without sugar (A) and an NCD™ formulation comprising sugar (B). The particulate aggregates are observed in (A) but not in (B).
Figure 8B:
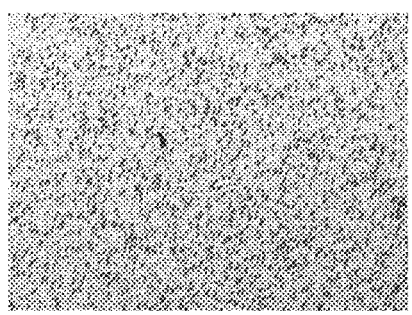

FIG. 7 shows a magnified image of the nanoparticulate meloxicam dispersion after it was filtered through an 8 μm filter at 200× magnification. Only 6 flake-like particulates were counted on filter ranging from 10-25 μm.

Example 4

The purpose of this example was to screen nanoparticulate meloxicam formulations comprising sucrose and/or mannitol for the stability of meloxicam particle size and particulate matter.

tested for particle size and particulate matter. The results are summarized in Tables 3 and 4, respectively.

TABLE 3

| Formulation | Storage Time Days | Condition °C. | Dmean nm | D50 nm | D90 nm |
|---|---|---|---|---|---|
| 2.5% meloxicam, 0.5% PVP K-17, 0.25% NaDOC, 5% Sucrose | 90 | 5 | 109 | 93 | 189 |
| | 90 | 25 | 114 | 96 | 199 |
| | 90 | 40 | 118 | 101 | 204 |
| 2.5% meloxicam, 0.5% PVP K-17, 1.25% Sucrose, 1.25% Mannitol | 90 | 5 | 156 | 141 | 230 |
| | 90 | 25 | 155 | 142 | 227 |
| | 90 | 40 | 162 | 149 | 235 |
| 2.5% meloxicam, 0.5% PVP K-17, 2.5% Mannitol, 0.25% NaDOC | 90 | 5 | 96 | 94 | 122 |
| | 90 | 25 | 99 | 95 | 127 |
| 2.5% meloxicam, 0.5% PVP K-17, 1.25% Sucrose, 1.25% Mannitol, 0.25% NaDOC | 90 | 5 | 92 | 91 | 114 |
| | 90 | 25 | 94 | 92 | 117 |
| | 90 | 40 | 98 | 95 | 126 |

TABLE 4

| Formulation | Storage Time Days | Condition °C. | Particles Observed (100 GFOV)* | Approx. Particles Retained on 47 mm Filter |
|---|---|---|---|---|
| 2.5% meloxicam, 0.5% PVP K-17, 2.5% Mannitol, 0.25% NaDOC | 7 | 5 | 37 | 642 |
| | 7 | 25 | 52 | 902 |
| | 7 | 40 | 204/165** | 3539/2863** |
| 2.5% meloxicam, 0.5% PVP K-17, 1.25% Sucrose, 1.25% Mannitol, 0.25% NaDOC | 7 | 25 | 75 | 1301 |
| | 7 | 40 | 16 | 278 |

*Graticule Field of View.
**Results obtained by two different analysts

Meloxicam formulations were milled in the presence of sucrose and/or mannitol on a DynoMill. After 7 to 90 days of storage at 5° C., 25° C. or 40° C., the formulations were It appeared that including sucrose and/or mannitol was able to reduce the flake-like aggregation in the formulations. Further screening studies were performed to determine the type and concentration of sugar in the formulations.

Additional meloxicam formulations were milled using either a DynoMill with a 150 mL chamber or a NanoMill-01 with a 100 mL chamber. The formulations comprising 2.5% meloxicam were stored at 5° C., 25° C. or 40° C. for up to 3 months and counted for particulate matter. The results are summarized in Table 5.

TABLE 5

| Sample | PVP (%) | NaDOC (%) | Sucrose (%) | Mannitol (%) | Storage Temp. (° C.) | Particulate Counts | | | | |
|---|---|---|---|---|---|---|---|---|---|---|
| | | | | | | initial | 1 wk | 2 wks | 1 mon | 3 mons |
| 1 | 0.5 K17 | 0.25 | 10 | 0 | 5 | 243 | | 1006 | 1666 | 109 |
| | | | | | 25 | | | 156 | 17 | 32 |
| | | | | | 40 | | | 35 | 87 | 71 |
| 2 | 0.5 K17 | 0.25 | 5 | 0 | 5 | 295 | | 746 | 191 | 57 |
| | | | | | 25 | | | 69 | 69 | 121 |
| | | | | | 40 | | | 69 | 555 | 116 |
| 3 | 0.5 K17 | 0.25 | 2.5 | 0 | 5 | 850 | | 2307 | 208 | 148 |
| | | | | | 25 | | | 451 | 208 | 52 |
| | | | | | 40 | | | 226 | 121 | 74 |
| 4 | 0.5 K17 | 0.25 | 1.25 | 0 | 5 | 1024 | | 87 | 330 | 89 |
| | | | | | 25 | | | 69 | 17 | 35 |
| | | | | | 40 | | | 52 | 347 | 69 |
| 5 | 0.5 K17 | 0.25 | 0 | 5 | 5 | 937 | | 382 | 590 | 69 |
| | | | | | 25 | | | 87 | 139 | 102 |
| | | | | | 40 | | | 52 | 295 | 992 |
| 6 | 0.5 K17 | 0.25 | 0 | 2.5 | 5 | 104 | | 416 | 1284 | 63 |
| | | | | | 25 | | | 330 | 139 | 119 |
| | | | | | 40 | | | 382 | 278 | 104 |
| 7 | 0.5 K17 | 0.25 | 0 | 1.25 | 5 | 243 | | 1006 | 87 | 60 |
| | | | | | 25 | | | 52 | 468 | 29 |
| | | | | | 40 | | | 1284 | 2082 | 81 |
| 8 | 0.75 K12 | 0.25 | 10 | 0 | 5 | n/a | 1 | 7 | 56 | 23 |
| | | | | | 25 | | 27 | 4 | 174 | 13 |
| | | | | | 40 | | 13 | 9 | 34 | 10 |
| 9 | 0.5 K12 | 0.25 | 0 | 0 | 5 | n/a | | 9368 | | |
| | | | | | 25 | | | 5569 | | |
| | | | | | 40 | | | 12665 | | |
| 10 | 0.5 K17 | 0.25 | 0 | 0 | 5 | 541 | 19015 | | | |
| | | | | | 25 | | 87 | | | |
| | | | | | 40 | | 3886 | | | |
| 11 | 0.75 K12 | 0.25 | 0 | 0 | 5 | 3834 | 399 | | | |
| | | | | | 25 | | 6679 | | | |
| | | | | | 40 | | 573 | | | |

Example 5

The purpose of this example was to demonstrate the suitability of nanoparticulate meloxicam formulations for a sterile filtration process, and thus suitable for parenteral use.

Formulations comprising 2.5% meloxicam were milled in the presence of 0.5% PVP K17 or 0.75% PVP K12 and two different concentrations of sucrose where successfully filtered through a sterilizing grade filter. The amount of filtered material is indicative of a pilot scale process. The test conditions and results are summarized in Table 6.

TABLE 6

| API (%) | PVP K-12 (%) | PVP K-17 (%) | Sucrose (%) | NaDOC (%) | Mean PS (nm) | Amount filtered |
|---|---|---|---|---|---|---|
| 2.50 | — | 0.50 | 10.0 | 0.25 | 72 | 1200 g |
| 2.50 | — | 0.50 | 10.0 | 0.25 | 112 | >5000 g |
| 2.50 | — | 0.50 | 10.0 | 0.25 | 139 | >5000 g |
| 2.50 | 0.75 | — | 10.0 | 0.25 | 139 | >5000 g |

The formulations comprising 0.5% PVP K17 showed no difference in filterability from the formulations comprising 0.75% PVP K12.

Example 10

The purpose of this example was to evaluate the stability of meloxicam formulations with different pH levels in terms of meloxicam particle size and particulate matter.

A slurry of 15% meloxicam and 3% PVP K17 was milled on a DynoMill at 89% media load at a speed of 4200 rpm for 60 minutes. 0%, 0.75% or 1.5% of NaDOC was included in the milling slurry. Sodium phosphate buffers at a concentration of 50 mM, 100 mM, 125 mM or 200 mM and at a pH level of pH 6.0, 7.5 and 9.0 were used to adjust the pH of the formulations. Alternatively, potassium phosphate, such as potassium phosphate/NaOH at pH 7.5 was used. The formulations were generally adjusted with sodium phosphate buffers unless otherwise noted.

The obtained nanoparticulate meloxicam dispersion was diluted to the final concentration of 2.5% meloxicam, 0.5% PVP K17 with sterile water for injection or with additional buffer. The stability results are summarized in Table 7.

TABLE 7

| Buffer Conc (mM) | % NaDOC (Slurry) | NCD pH | Dmean (nm) | Particulate Count (unfiltered) | Particle count/10 mL* |
|---|---|---|---|---|---|
| 200 | 1.5 | 7.6 | 129 | 5/20 ml | 2 |
| 125 | 0.75 | 7.4 | 119 | 15/20 ml | 8 |
| 50 | 1.5 | 6.5 | 102 | 168/20 ml | 84 |
| 50 | 0 | 5.7 | 113 | TNTC/150 ml | TNTC |
| 125 | 0 | 7 | 123 | 46/225 ml | 2 |

TABLE 7-continued

| Buffer Conc (mM) | % NaDOC (Slurry) | NCD pH | Dmean (nm) | Particulate Count (unfiltered) | Particle count/10 mL* |
|---|---|---|---|---|---|
| 200 | 1.5 | 6.2 | 106 | TNTC/20 ml | TNTC |
| ** | 0.5 | 7.2 | 115 | 137/20 ml | 68 |

*Normalized to count/10 mL from previous column
** pH was adjusted with potassium phosphate/NaOH In general, samples with pH above 7 returned the lowest initial particulate counts, from 2 to 68 per 10 ml sample; while the samples having a pH of 6.5 or less had the highest particulate counts, from 84 to too numerous to count per 10 mL of sample.

Two exemplary formulations with superior properties were identified:
(1) a formulation comprising 2.5% meloxicam, 0.5% PVP K17, and 0.125% NaDOC in buffer pH 7.5 at 125 mM, yielding a final NCD pH of 7.4. The particulate count was 15 flakes per 20 mL and
(2) a formulation comprising 2.5% meloxicam, 0.5% PVP K17, and 0.25% NaDOC in buffer pH 9 at 200 mM, yielding a final NCD pH of 7.6. The particulate count was 5 per 20 mL of sample.

What is claimed is:

1. A method of reducing flake-like aggregates in an injectable nanoparticulate meloxicam composition, comprising:
   (a) preparing a dispersion of nanoparticulate meloxicam and at least one surface stabilizer, wherein the dispersion comprises meloxicam particles having an effective average particle size of less than about 2000 nm, at least one surface stabilizer, and a liquid in which the meloxicam particles are poorly soluble; and
   (b) adding a flake-like aggregation reducing agent selected from (i) a buffer selected from the group consisting of a phosphate buffer, an acetate buffer, a citrate buffer, a sodium phosphate buffer a potassium phosphate buffer, and a sodium acetate buffer resulting in the composition having a pH above about 7.0, and (ii) a sugar selected from the group consisting of sucrose, mannitol and dextrose to the nanoparticulate meloxicam dispersion of step (a), wherein the resultant composition is suitable for injectable administration.

2. The method of claim 1, wherein the flake-like aggregation reducing agent is a buffer selected from the group consisting of a phosphate buffer, an acetate buffer, a citrate buffer, a sodium phosphate buffer, a potassium phosphate buffer, and a sodium acetate buffer.

3. The method of claim 1, wherein the flake-like aggregation reducing agent is a sugar selected from the group consisting of sucrose, mannitol and dextrose.

4. The method of claim 1, wherein the meloxicam has an effective average particle size selected from the group consisting of less than about 1900 nm, less than about 1800 nm, less than about 1700 nm, less than about 1600 nm, less than about 1500 nm, less than about 1400 nm, less than about 1300 nm, less than about 1200 nm, less than about 1100 nm, less than about 1000 nm, less than about 900 nm, less than about 800 nm, less than about 700 nm, less than about 600 nm, less than about 500 nm, less than about 400 nm, less than about 300 nm, less than about 250 nm, less than about 200 nm, less than about 150 nm, less than about 100 nm, less than about 75 nm, and less than about 50 nm.

5. The method of claim 1, wherein the injectable nanoparticulate meloxicam composition comprises no more than 6,000 meloxicam particles that are greater than 10 µm in size and no more than 600 meloxicam particles that are greater than 25 µm in size.

6. The method of claim 1, wherein the injectable nanoparticulate meloxicam composition comprises no more than 3,000 meloxicam particles that are greater than 10 µm in size and no more than 300 meloxicam particles that are greater than 25 µm in size.

7. The method of claim 1, wherein the injectable nanoparticulate meloxicam composition has fewer than about 1000 meloxicam particles larger than 25 µm, fewer than about 900 meloxicam particles larger than 25 µm, fewer than about 800 meloxicam particles larger than 25 µm, fewer than about 700 meloxicam particles larger than 25 µm, fewer than about 600 meloxicam particles larger than 25 µm, fewer than about 500 meloxicam particles larger than 25 µm, fewer than about 400 meloxicam particles larger than 25 µm, fewer than about 300 meloxicam particles larger than 25 µm, fewer than about 250 meloxicam particles larger than 25 µm, fewer than about 200 meloxicam particles larger than 25 µm, fewer than about 150 meloxicam particles larger than 25 µm, fewer than about 100 meloxicam particles larger than 25 µm, or fewer than about 50 meloxicam particles larger than 25 µm.

8. The method of claim 1, wherein the injectable nanoparticulate meloxicam composition has fewer than about 10,000 meloxicam particles larger than 10 µm, fewer than about 9000 meloxicam particles larger than 10 µm, fewer than about 8000 meloxicam particles larger than 10 µm, fewer than about 7000 meloxicam particles larger than 10 µm, fewer than about 6000 meloxicam particles larger than 10 µm, fewer than about 5000 meloxicam particles larger than 10 µm, fewer than about 4000 meloxicam particles larger than 10 µm, fewer than about 3000 meloxicam particles larger than 10 µm, fewer than about 2000 meloxicam particles larger than 10 µm, or fewer than about 1000 meloxicam particles larger than 10 µm.

9. The method of claim 1, wherein the surface stabilizer is selected from the group consisting of a non-ionic surface stabilizer, an ionic surface stabilizer, an anionic surface stabilizer, a cationic surface stabilizer, and a zwitterionic surface stabilizer.

10. The method of claim 1, wherein the surface stabilizer is selected from the group consisting of cetyl pyridinium chloride, gelatin, casein, phosphatides, dextran, glycerol, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, dodecyl trimethyl ammonium bromide, polyoxyethylene stearates, colloidal silicon dioxide, phosphates, sodium dodecyl sulfate, carboxymethylcellulose calcium, hydroxypropyl celluloses, hypromellose, carboxymethylcellulose sodium, methylcellulose, hydroxyethylcellulose, hypromellose phthalate, noncrystalline cellulose, magnesium aluminum silicate, triethanolamine, polyvinyl alcohol, polyvinylpyrrolidone, 4-(1,1,3,3-tetramethylbutyl)-phenol polymer with ethylene oxide and formaldehyde, poloxamers; poloxamines, a charged phospholipid, dioctylsulfosuccinate, dialkylesters of sodium sulfosuccinic acid, sodium lauryl sulfate, alkyl aryl polyether sulfonates, mixtures of sucrose stearate and sucrose distearate, p-isononylphenoxypoly-(glycidol), decanoyl-N-methylglucamide; n-decyl β-D-glucopyranoside; n-decyl β-D-maltopyranoside; n-dodecyl β-D-glucopyranoside; n-dodecyl β-D-maltoside, heptanoyl-N-methylglucamide; n-heptyl-β-D-glucopyranoside; n-heptyl β-D- thioglucoside; n-hexyl β-D-glucopyranoside; nonanoyl-N-methylglucamide; n-noyl β-D-glucopyranoside; octanoyl-N-methylglucamide; n-octyl-β-D-glucopyranoside; octyl β-D-thioglucopyranoside; lysozyme, PEG-phospholipid, PEG-cholesterol, PEG-cholesterol derivative, PEG-vitamin A, random copolymers of vinyl acetate and vinyl pyrrolidone, a cationic polymer, a cationic biopolymer, a cationic polysaccharide, a cationic cellulosic, a cationic alginate, a cationic nonpolymeric compound, a cationic phospholipids, cationic lipids, polymethylmethacrylate trimethylammonium bromide, sulfonium compounds, polyvinylpyrrolidone-2-dimethylaminoethyl methacrylate dimethyl sulfate, hexadecyltrimethyl ammonium bromide, phosphonium compounds, quaternary ammonium compounds, benzyl-di (2-chloroethyl)ethylammonium bromide, coconut trimethyl ammonium chloride, coconut trimethyl ammonium bromide, coconut methyl dihydroxyethyl ammonium chloride, coconut methyl dihydroxyethyl ammonium bromide, decyl triethyl ammonium chloride, decyl dimethyl hydroxyethyl ammonium chloride, decyl dimethyl hydroxyethyl ammonium chloride bromide, $C_{12-15}$dimethyl hydroxyethyl ammonium chloride, $C_{12-15}$dimethyl hydroxyethyl ammonium chloride bromide, coconut dimethyl hydroxyethyl ammonium chloride, coconut dimethyl hydroxyethyl ammonium bromide, myristyl trimethyl ammonium methyl sulphate, lauryl dimethyl benzyl ammonium chloride, lauryl dimethyl benzyl ammonium bromide, lauryl dimethyl (ethenoxy)$_4$ ammonium chloride, lauryl dimethyl (ethenoxy)$_4$ ammonium bromide, N-alkyl ($C_{12-18}$)dimethylbenzyl ammonium chloride, N-alkyl ($C_{14-18}$)dimethyl-benzyl ammonium chloride, N-tetradecylidmethylbenzyl ammonium chloride monohydrate, dimethyl didecyl ammonium chloride, N-alkyl and ($C_{12-14}$) dimethyl 1-napthylmethyl ammonium chloride, trimethylammonium halide, alkyl-trimethylammonium salts, dialkyl-dimethylammonium salts, lauryl trimethyl ammonium chloride, ethoxylated alkyamidoalkyldialkylammonium salt, an ethoxylated trialkyl ammonium salt, dialkylbenzene dialkylammonium chloride, N-didecyldimethyl ammonium chloride, N-tetradecyldimethylbenzyl ammonium, chloride monohydrate, N-alkyl($C_{12-14}$) dimethyl 1-naphthylmethyl ammonium chloride, dodecyldimethylbenzyl ammonium chloride, dialkyl benzenealkyl ammonium chloride, lauryl trimethyl ammonium chloride, alkylbenzyl methyl ammonium chloride, alkyl benzyl dimethyl ammonium bromide, $C_{12}$ trimethyl ammonium bromides, $C_{15}$ trimethyl ammonium bromides, $C_{17}$ trimethyl ammonium bromides, dodecylbenzyl triethyl ammonium chloride, poly-diallyldimethylammonium chloride, dimethyl ammonium chlorides, alkyldimethylammonium halogenides, tricetyl methyl ammonium chloride, decyltrimethylammonium bromide, dodecyltriethylammonium bromide, tetradecyltrimethylammonium bromide, methyl trioctylammonium chloride, tetrabutylammonium bromide, benzyl trimethylammonium bromide, choline esters, benzalkonium chloride, stearalkonium chloride compounds, cetyl pyridinium bromide, cetyl pyridinium chloride, halide salts of quaternized polyoxyethylalkylamines, alkyl pyridinium salts; amines, amine salts, amine oxides, imide azolinium salts, protonated quaternary acrylamides, methylated quaternary polymers, and cationic guar.

11. The method of claim 1, wherein the meloxicam is in a phase selected from the group consisting of a crystalline phase, an amorphous phase, a semi-crystalline phase, and any combination thereof.

12. The method of claim 1, wherein step (a) and step (b) are performed simultaneously.

13. The method of claim 1, wherein step (a) and step (b) are performed sequentially.

14. The method of claim 1, wherein the injectable nanoparticulate meloxicam composition further comprises one or more excipients.

15. The method of claim 14, wherein the one or more excipients is selected from the group consisting of binding agents, filling agents, lubricating agents, suspending agents, sweeteners, flavoring agents, preservatives, wetting agents and disintegrants.

* * * * *